United States Patent
Vougioukalakis et al.

(10) Patent No.: US 8,039,566 B2
(45) Date of Patent: Oct. 18, 2011

(54) OLEFIN METATHESIS INITIATORS BEARING THIAZOL-2-YLIDENE LIGANDS

(75) Inventors: Georgios C. Vougioukalakis, Crete (GR); Robert H. Grubbs, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 73 days.

(21) Appl. No.: 12/515,702

(22) PCT Filed: Nov. 20, 2007

(86) PCT No.: PCT/US2007/085239
§ 371 (c)(1),
(2), (4) Date: Feb. 1, 2010

(87) PCT Pub. No.: WO2008/064223
PCT Pub. Date: May 29, 2008

(65) Prior Publication Data
US 2010/0144987 A1    Jun. 10, 2010

Related U.S. Application Data

(60) Provisional application No. 60/860,443, filed on Nov. 21, 2006, provisional application No. 60/901,621, filed on Feb. 13, 2007, provisional application No. 60/896,726, filed on Mar. 23, 2007.

(51) Int. Cl.
*C08G 61/06* (2006.01)
*C07F 15/00* (2006.01)
*C07C 69/74* (2006.01)

(52) U.S. Cl. .......... 526/172; 548/103; 556/21; 556/136; 560/127; 560/261; 585/366; 585/643

(58) Field of Classification Search .............. 548/103; 556/21, 136; 526/172; 585/366, 643; 560/127, 560/261
See application file for complete search history.

(56) References Cited

U.S. PATENT DOCUMENTS

| 6,525,125 B1 | 2/2003 | Giardello et al. |
| 7,034,096 B2 | 4/2006 | Choi et al. |
| 7,687,635 B2 * | 3/2010 | Verpoort et al. .............. 548/103 |

FOREIGN PATENT DOCUMENTS

| WO | 03/087167 A2 | 10/2003 |
| WO | 2005/094345 A2 | 10/2005 |

OTHER PUBLICATIONS

Green et al, Chemistry of the Metal Carbonyls . . . Carbene(tetracarbonyl)-iron and -osmium Complexes containing Thiazolidinylidene and Related Ligands, J.C.S. Dalton: Inorg. Chem. (1972-1999) (1975), 10, 939-43.*

* cited by examiner

*Primary Examiner* — Fred M Teskin
(74) *Attorney, Agent, or Firm* — Nixon Peabody LLP; Jeffrey L. Costellia

(57) ABSTRACT

This invention relates to olefin metathesis catalysts general formula (I):

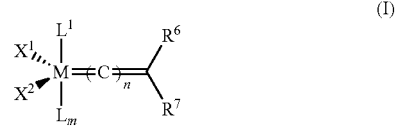

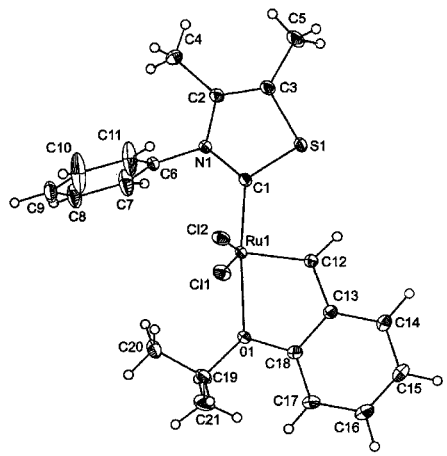

CRYSTAL STRUCTURE OF CATALYST 1 having a thiazol-2-ylidene ligand of general formula (II):
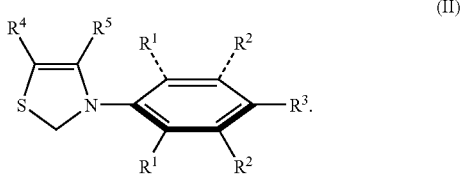
(II)
The catalysts have been found to be particularly good initiators of (a) ring-closing metathesis reactions used to prepare tetra-substituted cyclic olefins, and (b) cross-metathesis reactions used to prepare tri-substituted and di-substituted olefins.
33 Claims, 22 Drawing Sheets

CRYSTAL STRUCTURE OF CATALYST 1

CRYSTAL STRUCTURE OF CATALYST 2

CRYSTAL STRUCTURE OF CATALYST 3

CRYSTAL STRUCTURE OF CATALYST 3

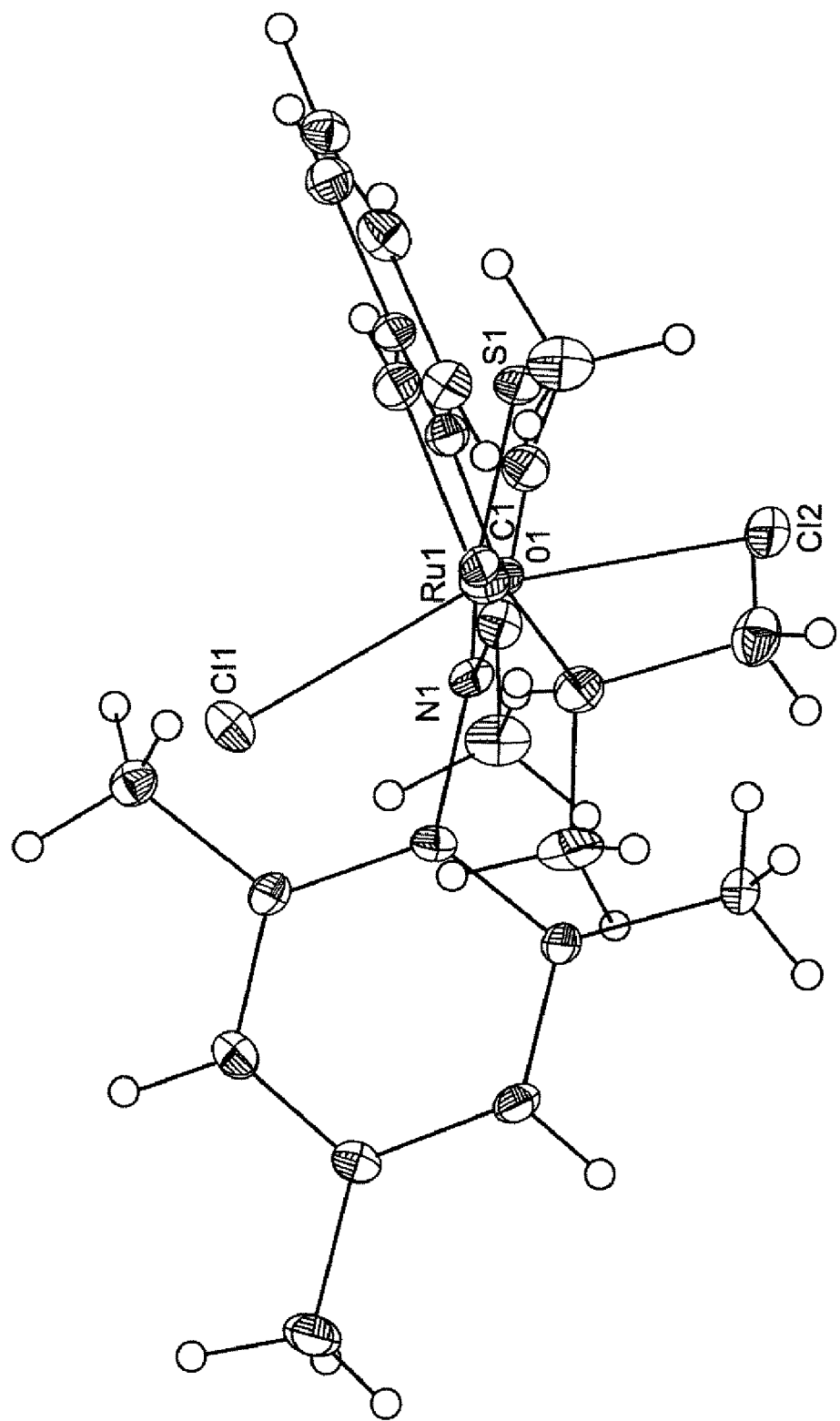
FIG. 3c CRYSTAL STRUCTURE OF CATALYST 3

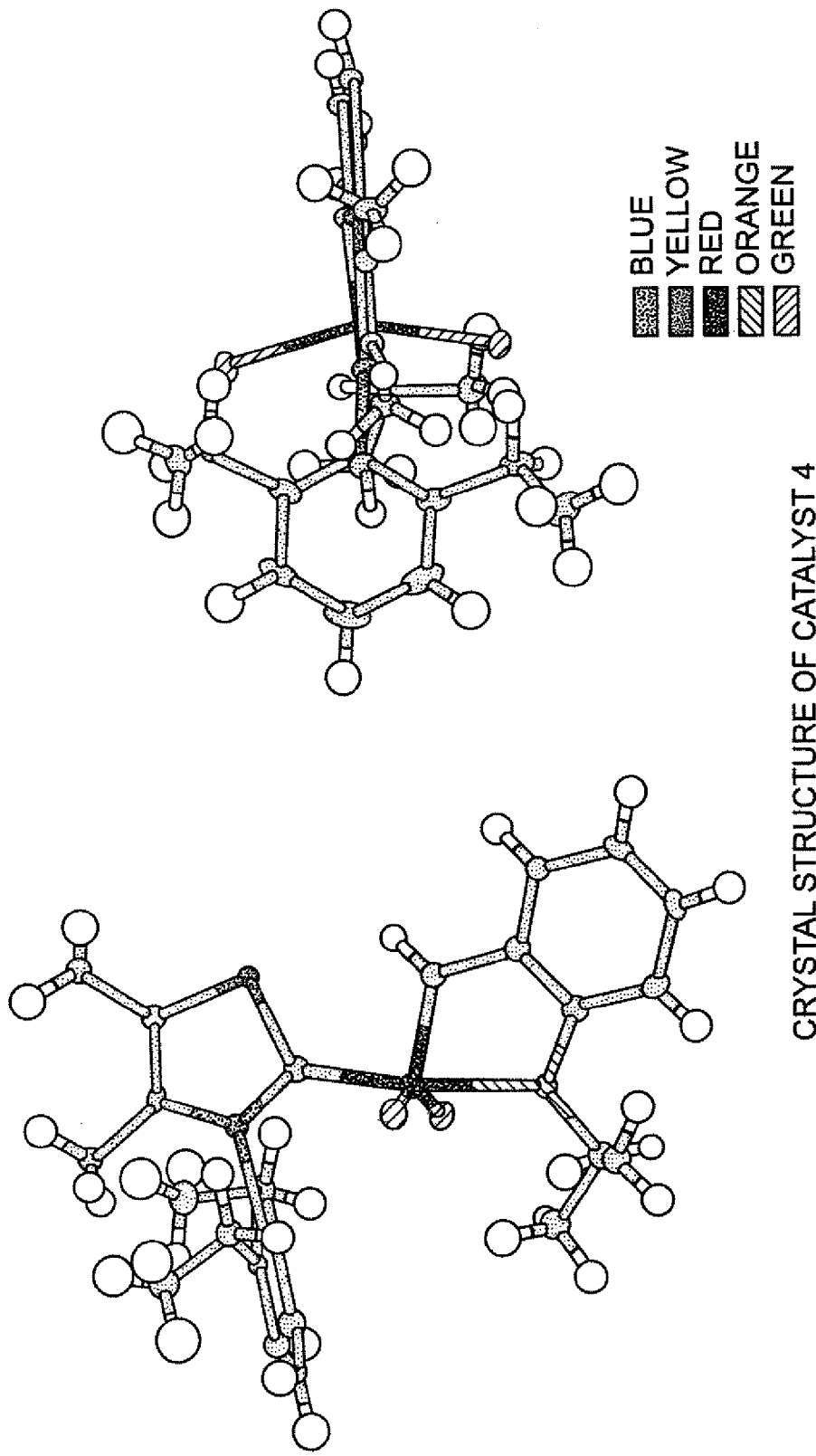
FIG. 4a CRYSTAL STRUCTURE OF CATALYST 4

CRYSTAL STRUCTURE OF CATALYST 4

OLEFIN METATHESIS INITIATORS BEARING THIAZOL-2-YLIDENE LIGANDS

PRIORITY STATEMENT

This application claims benefit to PCT Application No. PCT/US2007/085239, filed Nov. 20, 2007, which claims benefit to U.S. Provisional Application No. 60/860,443, filed Nov. 21, 2006; U.S. Provisional Application No. 60/901,621, filed Feb. 13, 2007; and U.S. Provisional Application No. 60/896,726, filed Mar. 23, 2007, all of which are herein incorporated by reference in their entirety.

The United States Government has certain rights in this invention pursuant to Grant No. N00014-03-1-0793 awarded by the Office of Naval Research.

BACKGROUND OF THE INVENTION

The development of well defined catalysts with good functional group tolerance has established olefin metathesis as a powerful tool for the formation of carbon-carbon double bonds. See Grubbs, R. H. *Handbook of Metathesis*; Wiley-VCH: Weinheim, Germany, 2003. Substitution of a phosphine for an N-heterocyclic carbene ligand, in ruthenium-based metathesis catalysts, led to more efficient complexes that maintain the high functional group tolerance and air and moisture stability of the phosphine-containing complexes. See for example, Schwab, P.; France, M. B.; Ziller, J. W.; Grubbs, R. H. *Angew. Chem., Int. Ed. Engl.* 1995, 34, 2039-2041; Schwab, P.; Grubbs, R. H.; Ziller, J. W. *J. Am. Chem. Soc.* 1996, 118, 100-110; or Scholl, M.; Ding, S.; Lee, C. W.; Grubbs, R. H. *Org. Lett.* 1999, 1, 953-956.

Nevertheless, the development of catalysts that could efficiently control E/Z selectivity in cross-metathesis reactions, or afford tetrasubstituted double bond products in ring-closing metathesis reactions, still represents a major challenge. Furthermore, catalysts more stable toward decomposition are always highly desired.

Thus, what is needed in the art is a catalyst that can accomplish these goals. This invention answers that need.

SUMMARY OF THE INVENTION

This invention relates to a compound having general formula (I):

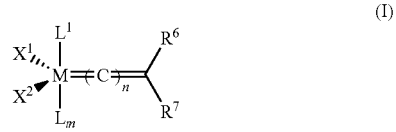

(I)

wherein M is Ru or Os; n is 0, 1 or 2; $X^1$ and $X^2$ are independently anionic ligands; L is any neutral 2-electron donor ligand; m is 1 or 2; and $L^1$ is a thiazol-2-ylidene ligand of formula (II):

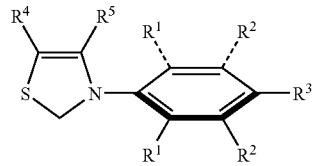

(II)

where $R^1$-$R^7$ are defined below.

The catalysts may be used in ring-closing metathesis reactions, cross-metathesis reactions, self-metathesis reactions, ring-opening metathesis polymerization reactions, and acyclic diene metathesis polymerization reactions.

The invention also relates to a method of preparing a tetra-substituted cyclic olefin through a ring-closing metathesis reaction. In the method, an olefinic compound that has at least two terminal olefins that are substituted at the beta-carbon of each terminal olefin is contacted with the above-described catalyst under metathesis conditions to form a cyclic tetra-substituted olefin.

The invention also relates to a method of preparing a tri-substituted olefin or a di-substituted olefin that is further substituted at the allylic carbon via a cross-metathesis reaction. In the method, two olefins are contacted with the above-described catalyst under metathesis conditions to form a tri-substituted olefin. The first olefin is monosubstituted at then-carbon and either unsubstituted or monosubstituted at the ∝-carbon. The second olefin is either disubstituted at the β-carbon or monosubstituted at the β-carbon with a further substitution at the allylic carbon, and either monosubstituted or unsubstituted at the ∝-carbon.

The invention also relates to a process for polymerizing cyclic olefins by contacting an cyclic olefin with the above-described catalyst.

BRIEF DESCRIPTION OF THE DRAWINGS

FIGS. 3(a)-3(c) depict the crystal structure of catalyst 3.
FIGS. 4(a)-4(b) depict the crystal structure of catalyst 4.

DESCRIPTION OF THE INVENTION

Figure 1:
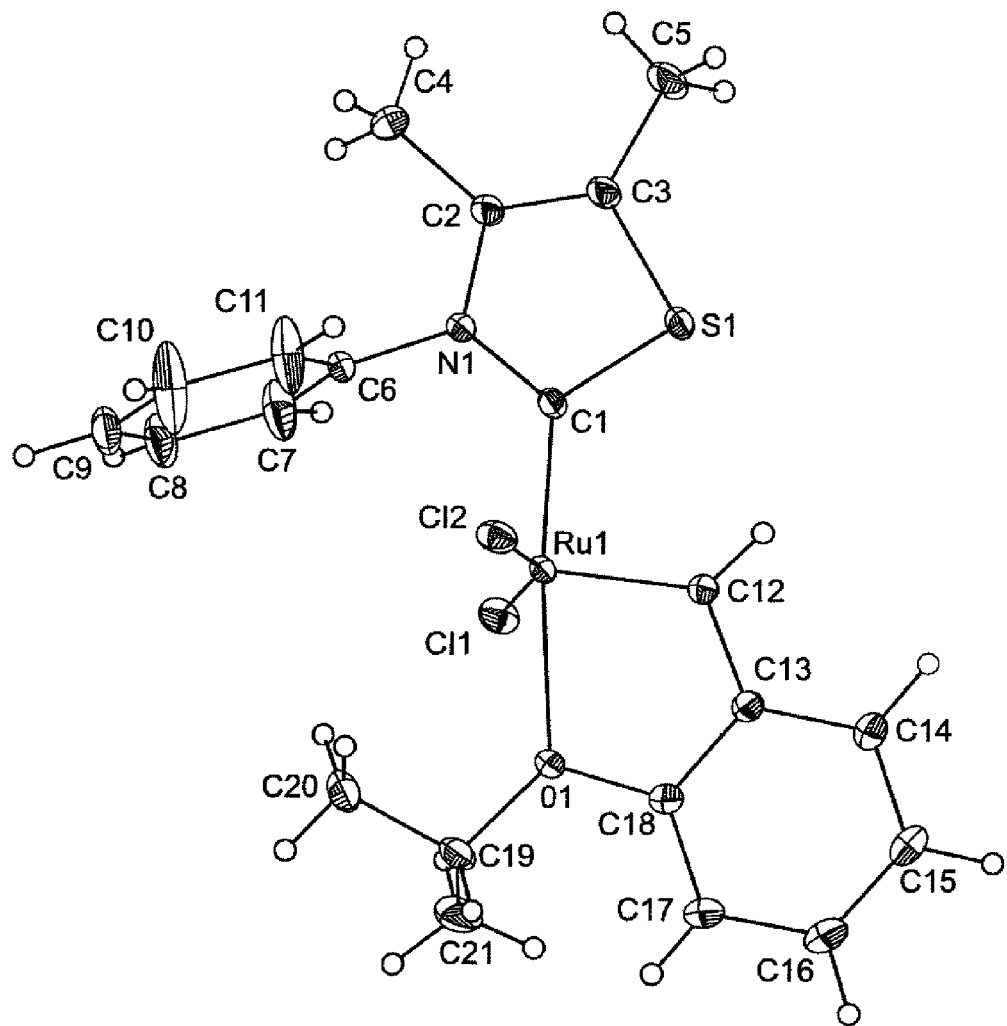
FIG. 1 depicts the crystal structure of catalyst 1.

The invention relates to the synthesis and the utility of N-heterocyclic carbene (NHC) olefin metathesis catalysts of general formula (I):

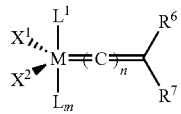

(I)

For catalysts of general formula (I), M is Ru or Os, and is preferably Ru.

In the catalysts of formula (I), $L^1$ is a thiazol-2-ylidene ligand of formula (II):

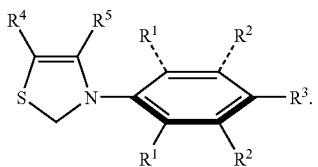

(II)

There are two combinations of $R^1$, $R^2$, and $R^3$ which define the substitution pattern on the phenyl ring bound to the nitrogen atom adjacent to the carbene carbon in the thiazol-2-ylidene ligands of formula (II). The combinations of $R^1$, $R^2$, and $R^3$ are:

a) each $R^1$ is independently a primary or secondary $C_1$-$C_4$ alkyl group; each $R^2$ is independently H, and $R^3$ is independently H, a substituted or unsubstituted $C_1$-$C_8$ alkyl group, substituted or unsubstituted phenyl, substituted or unsubstituted naphthyl, or substituted or unsubstituted anthracenyl, or a functional group selected from the group consisting of halo, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy; or b) each $R^1$ is H; each $R^2$ is independently H, a substituted or unsubstituted $C_1$-$C_8$ alkyl group, substituted or unsubstituted phenyl, substituted or unsubstituted naphthyl, or substituted or unsubstituted anthracenyl; and $R^3$ is H.

In combination a), $R^1$ is preferably methyl, ethyl, or iso-propyl. Each $R^3$ is preferably H, iso-butyl, tert-butyl, neopentyl, neohexyl, or phenyl and is most preferably H. In combination b), $R^2$ is preferably a secondary or tertiary $C_3$-$C_{10}$ alkyl or aryl; more preferably, iso-butyl, tert-butyl, neopentyl, neohexyl, or phenyl and most preferably tert-butyl. $R^3$ is preferably H, iso-butyl, tert-butyl, neopentyl, neohexyl, or phenyl and is most preferably H.

In the thiazol-2-ylidene ligands of Formula (II) used in the complexes of the invention, $R^4$ and $R^5$ are each independently H, a substituted or unsubstituted $C_1$-$C_8$ alkyl group, substituted or unsubstituted aryl, or, together with the carbons carrying them, form a substituted or unsubstituted, fused 4-8 membered carbocylic ring or a substituted or unsubstituted, fused aromatic ring. Preferably $R^4$ and $R^5$ are H, $C_1$-$C_4$ alkyl, or fused cyclohexyl or phenyl.

$X^1$ and $X^2$ are independently anionic ligands. Preferably, $X^1$ and $X^2$ are halide, or one of the following groups: $C_1$-$C_{20}$ alkyl, aryl, $C_1$-$C_{20}$ alkoxide, aryloxide, $C_3$-$C_{20}$ alkyldiketonate, aryldiketonate, $C_1$-$C_{20}$ carboxylate, arylsulfonate, $C_1$-$C_{20}$ alkylsulfonate, $C_1$-$C_{20}$ alkylthio, $C_1$-$C_{20}$ alkylsulfonyl, or $C_1$-$C_{20}$ alkylsulfinyl. Optionally, $X^1$ and $X^2$ may be substituted with one or more moieties selected from the group consisting of $C_1$-$C_{10}$ alkyl, $C_1$-$C_{10}$ alkoxy, and aryl which in turn may each be further substituted with one or more groups selected from halogen, $C_1$-$C_5$ alkyl, $C_1$-$C_5$ alkoxy, and phenyl. In more preferred embodiments, $X^1$ and $X^2$ are halide, benzoate, $C_1$-$C_5$ carboxylate, $C_1$-$C_5$ alkyl, phenoxy, $C_1$-$C_5$ alkoxy, $C_1$-$C_5$ alkylthio, aryl, and $C_1$-$C_5$ alkyl sulfonate. As discussed below, the other ligands in a catalyst of the invention, when substituted, may also contain such substituents. In even more preferred embodiments, $X^1$ and $X^2$ are each halide, $CF_3CO_2$, $CH_3$, $CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate. In the most preferred embodiments, $X^1$ and $X^2$ are each chloride.

The variable "n" defines the number of successive double bounds in the alkylidene substituted by $R^6$ and $R^7$. The variable "n" is 0, 1 or 2. Preferably, "n" is 0.

$R^6$ and $R^7$ are each independently hydrogen or a substituted or unsubstituted group selected from the group consisting of $C_1$-$C_{20}$ alkyl, $C_2$-$C_{20}$ alkenyl, $C_2$-$C_{20}$ alkynyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ 20 alkylsulfonyl and $C_1$-$C_{20}$ alkylsulfinyl. Optionally, each of the $R^6$ or $R^7$ substituent group may be substituted with one or more moieties selected from the group consisting of $C_1$-$C_{10}$ alkyl, $C_1$-$C_{10}$ alkoxy, and aryl which in turn may each be further substituted with one or more groups selected from a halogen, a $C_1$-$C_5$ alkyl, $C_1$-$C_{15}$ alkoxy, and phenyl. Moreover, $R^6$ and $R^7$, as well as any other of the catalyst ligands, may further include one or more functional groups as long as they do not defeat the activity of the catalyst. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen. $R^6$ and $R^7$ may optionally be linked together to form a cyclic structure via one of the substituents mentioned above.

In preferred embodiments of these catalysts, the $R^6$ substituent is hydrogen, $C_1$-$C_5$ alkyl or aryl and the $R^7$ substituent is selected from the group consisting of $C_1$-$C_{20}$ alkyl, $C_2$-$C_{20}$ alkenyl, and aryl. In even more preferred embodiments, the $R^7$ substituent is phenyl or vinyl, optionally substituted with one or more moieties selected from the group consisting of $C_1$-$C_5$ alkyl, $C_1$-$C_5$ alkoxy, phenyl, and a functional group. In especially preferred embodiments. $R^7$ is phenyl or vinyl substituted with one or more moieties selected from the group consisting of chloride, bromide, iodide, fluoride, —$NO_2$, —$NMe_2$, methyl, methoxy and phenyl. In the most preferred embodiments, the $R^7$ substituent is phenyl or —C=C(CH$_3$)$_2$.

L may be any neutral 2-electron donor ligand known in the art. The variable "m" defines the number of neutral donor ligands, L. The variable "m" is 1 or 2 and preferably 1. When "m" is 1, L is any neutral 2-electron donor ligand. L may be linked to $R^7$ forming a chelating carbene ligand when "n" is zero. When "m" is 2, L is pyridine or substituted pyridine.

In a preferred embodiment, L is selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether. L may also represent the same ligand as $L^1$. In more preferred embodiments, L is a phosphine of the formula PR'R''R''', where R', R'', and R''' are each independently aryl; $C_1$-$C_{10}$ alkyl (in particular, a primary or secondary alkyl); or $C_3$-$C_6$ cycloalkyl. In the most preferred embodiments, L is selected from the group consisting of P(cyclohexyl)$_3$, P(cyclopentyl)$_3$, P(isopropyl)$_3$, and P(phenyl)$_3$.

In a preferred embodiment, L may be linked to $R^7$ forming a chelating carbene ligand. Chelating carbenes of this type are well-known in the art. When forming a chelating carbene ligand, n is zero. The L portion of the chelating carbene ligand is still a 2-electron donor ligand when linked to $R^7$. L may or may not be linked to $R^7$ through a spacer moiety. The spacer moiety may be substituted or unsubstituted. Preferably, $R^7$ is linked to L via spacer group being 2-5 atoms in length between L and $R^7$, for example via an alkyl group, a cycloalkyl group, or an aryl group. A preferred spacer group is a substituted or unsubstituted phenyl group.

U.S. Pat. Nos. 6,306,987; 6,620,955; 6,867,303; 6,921,735 and 7,026,495 as well published applications US 2003/0220512 A1, US 2004/0087438 A1 and US 2004/0176608 describe various chelating carbene ligands and are incorporated herein by reference as examples of how the ligand and R substituent on the carbene can be linked through various spacer moieties. Examples of ruthenium complexes with chelating carbene ligands, ligands linking the L ligand and the $R^7$ substitutent, are also described in Kingsbury, J. S.; Harrity, J. P. A.; Bonitatebus, P. J., Jr.; Hoveyda, A. H. *J. Am. Chem. Soc.* 1999, 121, 791 and Garber, S. B.; Kingsbury, J. S.; Gray, B. L.; Hoveyda, A. H. *J. Am. Chem. Soc.* 2000, 122, 8168.

Preferred catalysts of the invention where L and $R^7$ are linked include the following:

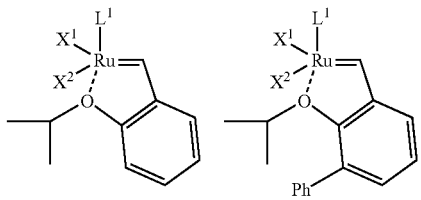

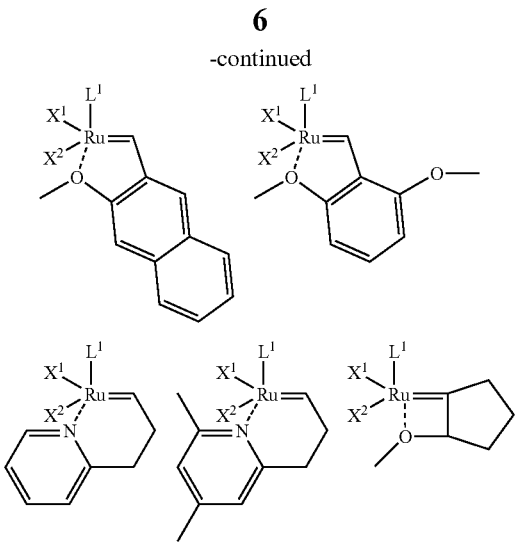

Preferred catalysts of formula (I) include catalyst A-C, shown in Chart 1 below. The dashed lines in the structures indicate that the coordinating ligand L may or may not be connected to the phenyl ring of the benzylidene. Catalysts where L is connected to the phenyl ring of the benzylidene represent preferred embodiments of the invention Catalysts 1-7 in Chart 2 are preferred catalysts within classes A-C.

Chart 1: Classes of olefin metathesis catalysts A, B and C.

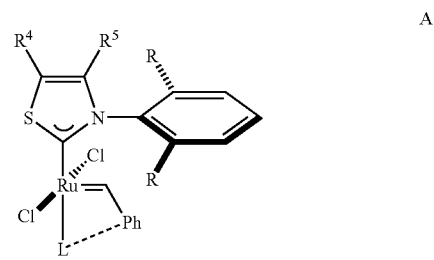

A

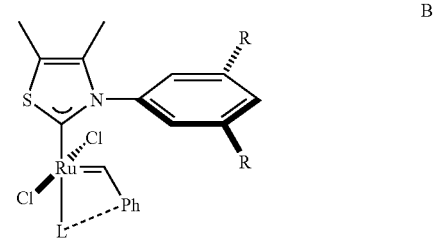

B

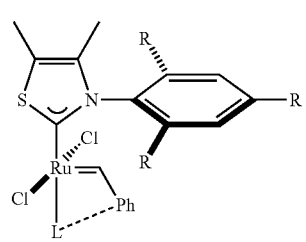

C

Chart 2: Ruthenium-based olefin metathesis catalysts 1-7

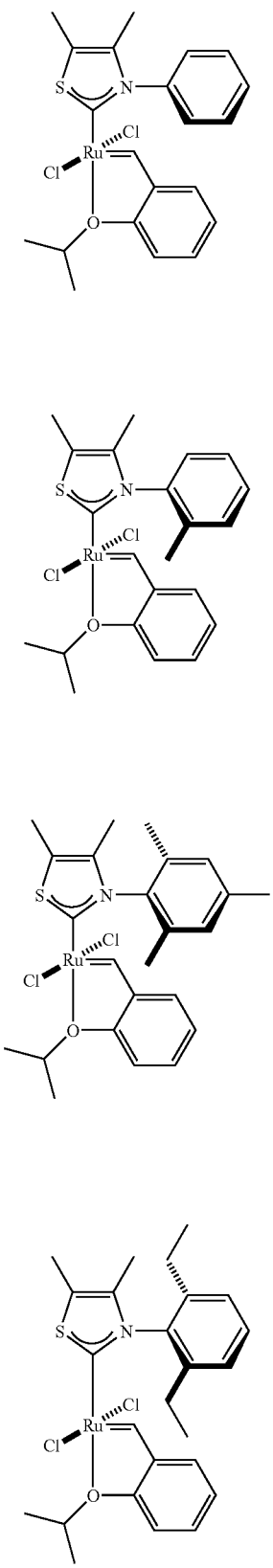

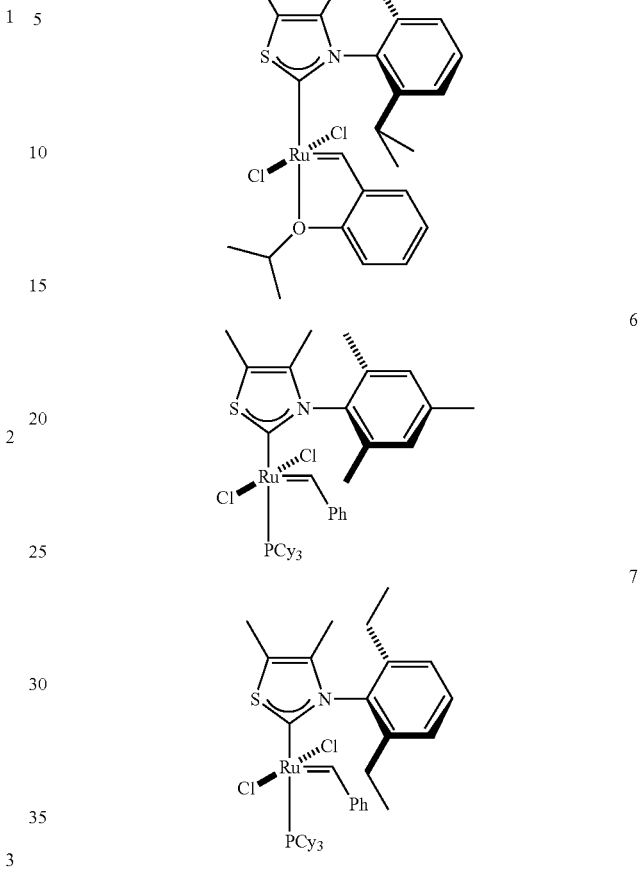

The PCy$_3$ analogs of 1 and 2 were also formed but are not stable and decompose in the reaction mixture. These PCy$_3$ analogs were only observed in situ.

Metathesis Reactions

The olefin metathesis catalysts of the invention are particularly efficient olefin metathesis catalysts. The catalysts efficiently control E/Z selectivity in cross-metathesis reactions, or afford tetrasubstituted double bond products in ring-closing metathesis reactions. Accordingly, one embodiment of the invention is an olefin metathesis reaction which contacts an olefin with an N-heterocyclic carbene (NHC) ruthenium olefin metathesis catalyst of the invention under metathesis conditions. The catalysts of the invention may be used in, for example, ring-closing metathesis (RCM), cross metathesis (CM), self metathesis (which is a type of cross metathesis), ring-opening metathesis polymerization (ROMP), and acyclic diene metathesis polymerization (ADMET). Additionally, the catalysts may be used to synthesize a variety of macrocyclic (seven-membered or higher) lactones, lactams, ketones, and ethers, some of which are alkaloids, perfume ingredients, and antibiotics, via macrocyclic RCM reactions of the corresponding α,ω-dienes.

U.S. Pat. Nos. 5,922,863 and 6,111,121, herein incorporated by reference in their entirety, disclose various RCM, CM, ROMP, and ADMET reactions using various metathesis catalysts. Those skilled in the art can readily identify the appropriate conditions for carrying out these reactions using the complexes of this invention.

The metathesis conditions for the catalysts of the invention are the same as those used in other olefin metathesis reactions and with other known olefin metathesis catalysts. Generally speaking, the olefin metathesis reactions are run at a temperature ranging from about 10° C. to about 70° C. and for a time period ranging from about 5 minutes to about 24 hours. The catalysts of the invention may be used in the same amounts as know for other olefin metathesis catalysts. Typically, about 1 to about 10 mol % of the catalyst is used and more often about 5 mol %.

The olefin metathesis catalysts of the invention are particularly useful in metathesis reactions for the production of tetra-substituted cyclic olefins. The catalysts of the invention have significantly increased efficiency/activity for the preparation of tetra-substituted cyclic olefins via olefin metathesis. To answer the need for more efficient preparation of such olefins another embodiment of the invention is a ring-closing metathesis method to prepare a tetra-substituted cyclic olefin. The method contacts an olefinic compound having at least two terminal olefins which are substituted at the beta-carbon of each terminal olefin with an N-heterocyclic carbene (NHC) olefin metathesis catalyst of the invention under metathesis conditions to form a cyclic tetra-substituted olefin.

A preferred group of olefinic compounds are those which have a structure according to general formula (III):

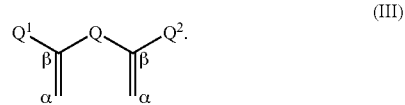

(III)

In general formula (III), Q is selected from hydrocarbylene, substituted hydrocarbylene, heteroatom-containing hydrocarbylene, and substituted heteroatom-containing hydrocarbylene. $Q^1$ and $Q^2$ are independently selected from hydrogen, hydrocarbyl, substituted hydrocarbyl, heteroatom-containing hydrocarbyl, substituted heteroatom-containing hydrocarbyl, and other groups such as halide, hydroxyl, sulfhydryl, cyano, cyanato, thiocyanato, amino, nitro, nitroso, sulfo, sulfonato, beryl, boron, phosphono, phosphonato, phosphinato, phospho, phosphino, and silyloxy. In the preparation of hindered cyclic olefins, both $Q^1$ and $Q^2$ cannot both be hydrogen and, more preferably, are both not hydrogen.

The catalysts are useful in cross-metathesis to prepare tri-substituted olefins, and di-substituted olefins which are further substituted at the allylic carbon. Accordingly, an embodiment of the invention relates to a cross-metathesis reaction in which an N-heterocyclic carbene (NHC) ruthenium olefin metathesis catalyst of the invention contacts two olefins under metathesis conditions. The first olefin is monosubstituted at the β-carbon and either unsubstituted or monosubstituted at the ∝-carbon. The second olefin is either disubstituted at the β-carbon or monosubstituted at the n-carbon but also has further substitution at the allylic carbon. Both olefins are either monosubstituted or unsubstituted at the ∝-carbon.

Examples of tri-substituted olefins are those having the formula $Q^1Q^2C=CHQ^3$. $Q^1$, $Q^2$, and $Q^3$ are independently selected from hydrocarbyl, substituted hydrocarbyl, heteroatom-containing hydrocarbyl, substituted heteroatom-containing hydrocarbyl, and other groups such as halide, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy. Any number of $Q^1$, $Q^2$, and $Q^3$ may also be linked as part of a cyclic olefin.

Di-substituted olefins are represented, for example, by the formula $Q^1Q^2C=CH_2$ or $Q^1HC=CHQ^2$. $Q^1$ and $Q^2$ are independently selected from hydrocarbyl, substituted hydrocarbyl, heteroatom-containing hydrocarbyl, substituted heteroatom-containing hydrocarbyl, and other groups such as halide, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy. $Q^1$ and $Q^2$ may also be linked in the case of cyclic olefins.

The formula $Q^1HC=CHCQ^2Q^3Q^4$ is representative of exemplary di-substituted olefins having further substitution at the allylic carbon. In this formula $Q^1$, $Q^2$, $Q^3$, and $Q^4$ are independently selected from hydrogen, hydrocarbyl, substituted hydrocarbyl, heteroatom-containing hydrocarbyl, substituted heteroatom-containing hydrocarbyl, and other groups such as halide, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy, provided that at least two of $Q^2$, $Q^3$ and $Q^4$ are different from hydrogen. $Q^1$, $Q^2$, $Q^3$, and $Q^4$ can be linked when the olefin is a cyclic olefin.

The term "hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms. The term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups such as discussed above, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups discussed above, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The following examples are intended to illustrate the invention. These examples should not be used to limit the scope of the invention, which is defined by the claims.

EXAMPLES

Example 1

Synthesis of the NHC Ligands for Catalysts 1-7

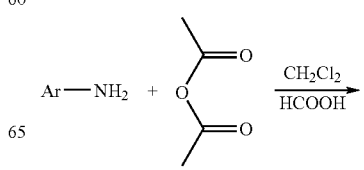

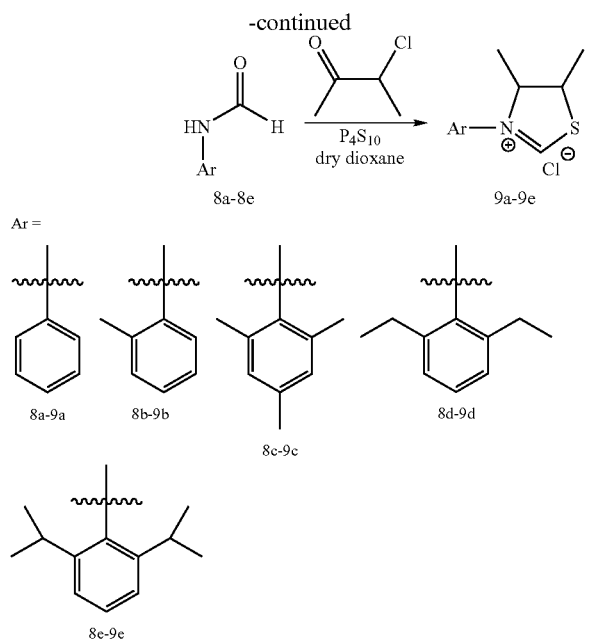

Example 1(a)

Preparation of 3-phenyl-4,5-dimethylthiazolium chloride 9a

A mixture of N-Formyl-aniline (8a, commercially available) (3.634 g, 30 mmol) and phosphorus pentasulfide (1.351 g, 3.04 mmol) in dry 1,4-dioxane (4 mL) was stirred at room temperature for 15 min under an argon atmosphere. 4-Chloro-2-butanone (2.131 g, 20 mmol) was added and the resulting slurry was heated at 100° C. The reaction mixture was refluxed for 50 min, initially becoming clear yellow and finally deep red. After cooling at room temperature, the crude mixture was diluted with $H_2O$ (20 mL). $Na_2CO_3$ was added to the reaction mixture until pH≈7. The solvent was evaporated under reduced pressure and the resulting solid was suspended in $CH_2Cl_2$ and purified by column chromatography (column packed with silica gel) eluting with $EtOH/CH_2Cl_2$ (15/85). Upon concentration of the last yellowish band, a viscous orange oil was obtained. This was solidified when washed under vigorous stifling with diethyl ether (3×2 mL) to afford 9a as a light pink solid (770 mg, 11%). $^1H$ NMR ($CD_2Cl_2$, 300 MHz): δ=11.13 (s, 1H), 7.67-7.60 (m, 3H), 7.53-7.49 (m, 2H), 2.57 (s, 3H), 2.23 (s, 3H); $^{13}C\{^1H\}$ NMR ($CD_2Cl_2$, 75 MHz): δ=161.03, 142.08, 141.75, 137.19, 132.10, 130.84, 126.34, 13.10, 12.86; HRMS ($FAB^+$) calculated for $C_{11}H_{12}NS$ $[M]^+$ 190.0690, observed 190.0693.

Example 1(b)

Preparation of 3-(2-methylphenyl)-4,5-dimethylthiazolium chloride 9b

A mixture of formic acid (14.361 g, 0.312 mol) and acetic anhydride (12.659 g, 0.124 mol) was stirred at room temperature for 1 h under an argon atmosphere. This mixture was added to a solution of 2-methylaniline (10.710 g, 0.1 mol) in dry dichloromethane (60 ml) at such a rate that the temperature of the reaction mixture was kept between 5 and 10° C. The reaction was stirred at room temperature for 16 h and then refluxed for 4 h. The solvent was evaporated under reduced pressure, the residue was dissolved in $CHCl_3$ (200 mL) and washed with a saturated aqueous $NaHCO_3$ solution (3×200 mL), and water (200 mL). The organic layer was dried over $Na_2SO_4$ and the solvent was evaporated under reduced pressure. The remaining yellow solid was washed with a mixture of hexanes/diethyl ether (2×10 mL) and then with hexanes (3×5 mL) to afford N-formyl-2-methylaniline 8b as a white solid (9.70 g, 72%). $^1H$ NMR ($CDCl_3$, 300 MHz): δ=9.03-8.18 (m, 2H, CHO, NH), 7.77-7.03 (m, 4H), 2.30-2.22 (m, 3H); $^{13}C\{^1H\}$NMR ($CDCl_3$, 75 MHz): δ=164.41, 160.32, 135.50, 134.99, 131.45, 130.82, 130.50, 129.87, 127.25, 126.80, 126.34, 125.84, 123.75, 121.32, 18.05, 17.99; HRMS ($FAB^+$) calculated for $C_8H_{10}NO$ $[M]^+$ 136.0762, observed 136.0783.

A mixture of 8b (4.055 g, 30 mmol) and phosphorus pentasulfide (1.351 g, 3.04 mmol) in dry 1,4-dioxane (4 mL) was stirred at room temperature for 15 min under an argon atmosphere. 4-Chloro-2-butanone (2.131 g, 20 mmol) was added and the resulting slurry was heated at 100° C. The reaction mixture was refluxed for 50 min, initially becoming clear yellow and finally deep red. After cooling at room temperature, the crude mixture was diluted with $H_2O$ (20 mL). $Na_2CO_3$ was added to the reaction mixture until pH≈7. The solvent was evaporated under reduced pressure and the resulting solid was suspended in $CH_2Cl_2$ and purified by column chromatography (column packed with silica gel) eluting with $EtOH/CH_2Cl_2$ (15/85). Upon concentration of the last yellowish band, a viscous orange oil was obtained. This was solidified when washed under vigorous stirring with diethyl ether (3×2 mL) to afford 9b as a tan solid (1.20 g, 17%). $^1H$ NMR ($CD_2Cl_2$, 300 MHz): δ=11.09 (s, 1H), 7.53-7.31 (m, 4H), 2.57 (s, 3H), 2.08 (s, 3H), 2.04 (s, 3H); $^{13}C\{^1H\}$ NMR ($CD_2Cl_2$, 75 MHz): δ=160.77, 142.05, 136.10, 134.60, 134.30, 132.23, 132.00, 128.08, 126.55, 17.23, 12.90, 11.98; HRMS ($FAB^+$) calculated for $C_{12}H_{14}NS$ $[M]^+$ 204.0847, observed 204.0845.

Example 1(c)

Preparation of 3-(2,4,6-trimethylphenyl)-4,5-dimethylthiazolium chloride 9c

A mixture of formic acid (14.361 g, 0.312 mol) and acetic anhydride (12.659 g, 0.124 mol) was stirred at room temperature for 1 h under an argon atmosphere. This mixture was added to a solution of 2,4,6-trimethylaniline (13.521 g, 0.1 mol) in dry dichloromethane (60 ml) at such a rate that the temperature of the reaction mixture was kept between 5 and 10° C. The reaction was stirred at room temperature for 16 h and then refluxed for 4 h. The solvent was evaporated under reduced pressure, the residue was dissolved in $CHCl_3$ (200 mL) and washed with a saturated aqueous $NaHCO_3$ solution (3×200 mL), and water (200 mL). The organic layer was dried over $Na_2SO_4$ and the solvent was evaporated under reduced pressure. The remaining yellow solid was washed with hot diethyl ether (2×50 mL) to afford N-formyl-2,4,6-trimethylaniline 8c[1] as a white solid (11.42 g, 70%). $^1H$ NMR ($CDCl_3$, 300 MHz): δ=8.39-8.03 (m, 1H, CHO), 7.26-6.91 (m, 2H), 6.75 (broad s, 1H, NH), 2.29-2.21 (m, 9H); $^{13}C\{^1H\}$ NMR ($CDCl_3$, 75 MHz): δ=165.48, 160.05, 137.75, 137.61, 135.37, 135.16, 130.92, 130.74, 129.53, 129.16, 21.15, 21.12, 18.84, 18.64; HRMS (FAB$^+$) calculated for $C_{10}H_{14}NO$ [M]$^+$ 164.1075, observed 164.1116.

[1] (a) Arduengo, A. J.; Goerlich, J. R.; Marshall, W. J. *Liehigs Ann./Recited* 1997, 365-374. (b) J. Liebscher, *Methoden der Organischen Chemie (Hauben-Weyl)* 4th ed. (Ed.: E. Schaumann), Georg Thieme Verlag, New York, 1994 Band E 8b, Heratrene III/Part 2, p. 48. (c) Hromatka, O. U.S. Pat. No. 2,160,867, 1939.

A mixture of 8c (4.897 g, 30 mmol) and phosphorus pentasulfide (1.351 g, 3.04 mmol) in dry 1,4-dioxane (10 mL) was stirred at room temperature for 15 min under an argon atmosphere. 4-Chloro-2-butanone (2.131 g, 20 mmol) was added and the resulting slurry was heated at 100° C. The reaction mixture was refluxed for 50 min, initially becoming clear yellow and finally deep red. After cooling at room temperature, the crude mixture was diluted with $H_2O$ (20 mL). $Na_2CO_3$ was added to the reaction mixture until pH≈7. The solvent was evaporated under reduced pressure and the resulting solid was suspended in $CH_2Cl_2$ and purified by column chromatography (column packed with silica gel) eluting with $EtOH/CH_2Cl_2$ (15/85). Upon concentration of the last yellowish band, a viscous yellow oil was obtained. This was solidified when washed under vigorous stirring with diethyl ether (3×2 mL) to afford 9e as a tan solid (1.33 g, 17%). $^1H$ NMR (CDCl$_3$, 300 MHz): δ=10.84 (s, 1H), 6.96 (s, 2H), 2.57 (s, 3H), 2.27 (s, 3H), 2.02 (s, 3H), 1.85 (s, 6H); $^{13}C\{^1H\}$ NMR (CDCl$_3$, 75 MHz): δ=160.81, 142.18, 141.58, 134.95, 133.65, 132.86, 130.36, 21.35, 17.57, 13.21, 11.62; HRMS (FAB$^+$) calculated for $C_{14}H_{18}NS$ [M]$^+$ 232.1160, observed 232.1158.

Example 1(d)

Preparation of
3-(2,6-diethylphenyl)-4,5-dimethylthiazolium chloride 9d

A mixture of formic acid (14.361 g, 0.312 mol) and acetic anhydride (12.659 g, 0.124 mol) was stirred at room temperature for 1 h under an argon atmosphere. This mixture was added to a solution of 2,6-diethylaniline (14.924 g, 0.1 mol) in dry dichloromethane (60 ml) at such a rate that the temperature of the reaction mixture was kept between 5 and 10° C. The reaction was stirred at room temperature for 16 h and then refluxed for 4 h. The solvent was evaporated under reduced pressure, the residue was dissolved in CHCl$_3$ (200 mL) and washed with a saturated aqueous NaHCO$_3$ solution (3×200 mL), and water (200 mL). The organic layer was dried over Na$_2$SO$_4$ and the solvent was evaporated under reduced pressure. The remaining yellow solid was washed with hot diethyl ether (2×50 mL) to afford N-formyl-2,6-diethylaniline 8d as a white solid (13.16 g, 74%). $^1H$ NMR (CDCl$_3$, 300 MHz): δ=8.15-8.02 (m, 1H, CHO), 7.86 (broad s, 1H, NH), 7.25-7.06 (m, 3H), 2.65 (q, J=7 Hz, 2H), 2.53 (q, J=7 Hz, 2H), 1.20 (t, J=7 Hz, 3H), 1.14 (t, J=7 Hz, 3H); $^{13}C\{^1H\}$ NMR (CDCl$_3$, 75 MHz): δ=165.97, 161.00, 142.13, 141.52, 132.15, 131.66, 128.65, 128.37, 127.09, 126.49, 25.18, 25.04, 15.00, 14.62; HRMS (EI$^+$) calculated for $C_{11}H_{15}NO$ [M]$^+$ 177.1154, observed 177.1159.

A mixture of 8d (3.545 g, 20 mmol) and phosphorus pentasulfide (0.900 g, 2.02 mmol) in dry 1,4-dioxane (5 mL) was stirred at room temperature for 15 min under an argon atmosphere. 4-Chloro-2-butanone (1.422 g, 20 mmol) was added and the resulting slurry was heated at 100° C. The reaction mixture was refluxed for 50 min, initially becoming clear yellow and finally deep red. After cooling at room temperature, the crude mixture was diluted with $H_2O$ (20 mL). $Na_2CO_3$ was added to the reaction mixture until pH≈7. The solvent was evaporated under reduced pressure and the resulting solid was suspended in $CH_2Cl_2$ and purified by column chromatography (column packed with silica gel) eluting with $EtOH/CH_2Cl_2$ (15/85). Upon concentration of the last band, a viscous brownish oil was obtained. This was solidified when washed under vigorous stirring with diethyl ether (3×2 mL) to afford 9d as a tan solid (560 mg, 10%). $^1H$ NMR (CDCl$_3$, 300 MHz): δ=10.97 (s, 1H), 7.52 (t, J=8 Hz, 1H), 7.30 (d, J=8 Hz, 2H), 2.63 (s, 3H), 2.16 (q, J=8 Hz, 4H), 2.06 (s, 3H), 1.14 (t, J=8 Hz, 6H); $^{13}C\{^1H\}$ NMR (CDCl$_3$, 75 MHz): δ=161.92, 141.63, 139.62, 135.04, 134.20, 132.30, 127.65, 23.97, 14.18, 13.16, 11.82; HRMS (FAB$^+$) calculated for $C_{15}H_{20}NS$ [M]$^+$ 246.1316, observed 246.1326.

Example 1(e)

Preparation of
3-(2,6-diisopropylphenyl)-4,5-dimethylthiazolium chloride 9e[2]

A mixture of formic acid (14.361 g, 0.312 mol) and acetic anhydride (12.659 g, 0.124 mol) was stirred at room temperature for 1 h under an argon atmosphere. This mixture was added to a solution of 2,6-diisopropylaniline (17.729 g, 0.1 mol) in dry dichloromethane (60 ml) at such a rate that the temperature of the reaction mixture was kept between 5 and 10° C. The reaction was stirred at room temperature for 16 h and then refluxed for 4 h. The solvent was evaporated under reduced pressure, the residue was dissolved in CHCl$_3$ (200 mL) and washed with a saturated aqueous NaHCO$_3$ solution (3×200 mL), and water (200 mL). The organic layer was dried over Na$_2$SO$_4$ and the solvent was evaporated under reduced pressure. The remaining yellow solid was recrystallized from diethyl ether (500 mL) to afford N-formyl-2,6-diisopropylaniline 8e[3] as a white solid (13.96 g, 68%). $^1H$ NMR (CDCl$_3$, 300 MHz): δ=8.47-8.01 (m, 1H, CHO), 7.36-7.18 (m, 3H), 6.79 (broad s, 1H, NH), 3.06-3.26 (m, 2H), 1.21 (d, J=7 Hz, 12H).

[2] (a) Arduengo, A. J.; Goerlich, J. R.; Marshall, W. J. *Liebigs Ann./Recueil* 1997, 365-374. (b) J. Liebscher, *Methoden der Organischen Chemie (Houben-Weyl)* 4th ed. (Ed.: E. Schaumann), Georg Thieme Verlag, New York, 1994 Band E 8b, Heratrene III/Part 2, p. 48. (c) Hromatka, O. U.S. Pat. No. 2,160,867, 1939.
[3] Kamer, P. C. J.; Nolte, R. J. M.; Drenth, W. *J. Am. Chem. Soc.* 1988, 110, 6818-6825.

A mixture of 8e (6.159 g, 30 mmol) and phosphorus pentasulfide (1.351 g, 3.04 mmol) in dry 1,4-dioxane (10 mL) was stirred at room temperature for 15 min under an argon atmosphere. 4-Chloro-2-butanone (2.131 g, 20 mmol) was added and the resulting slurry was heated at 100° C. The reaction mixture was refluxed for 1 h initially becoming clear yellow and finally deep red. After cooling at room temperature, the crude mixture was dissolved in $H_2O$ (350 mL) and washed with diethyl ether (3×150 mL). $Na_2CO_3$ was added to the aqueous phase until pH≈7. The solvent was evaporated under reduced pressure and the resulting solid was suspended in $CH_2Cl_2$ (50 mL) and filtered to remove undissolved inorganic salts. The solvent of the filtrate was evaporated under reduced pressure and the resulting red solid was recrystallized from ethanol-diethyl ether to afford 9e as a tan solid (690 mg, 11%). $^1$H-NMR (CDCl$_3$, 300 MHz): 11.08 (s, 1H), 7.59 (t, J=8 Hz, 1H), 7.36 (d, J=8 Hz, 2H), 2.65 (s, 3H), 2.09 (s, 3H), 2.03 (septet, J=7 Hz, 2H), 1.20 (d, J=7 Hz, 6H), 1.17 (d, J=7 Hz, 6H).

Example 2

Synthesis of Catalysts 1-7

Example 2(a)

Preparation of [RuCl$_2$(3-phenyl-4,5-dimethylthiazol-2-ylidene)(=CH-o-iPrO-Ph)] Catalyst 1

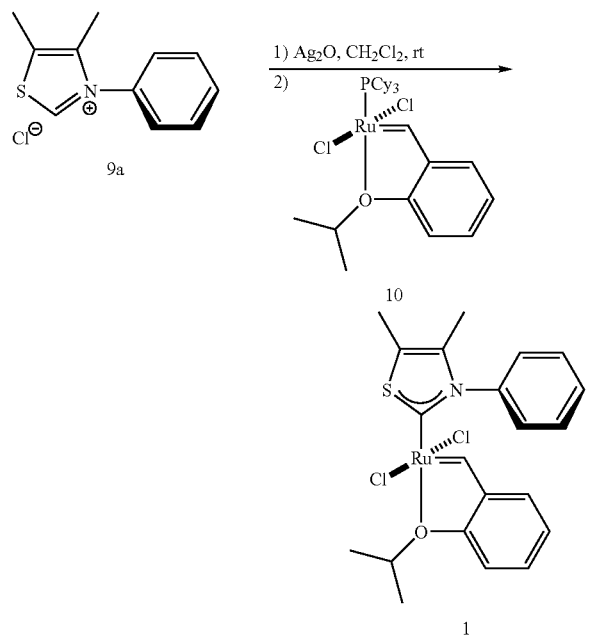

In a glove box, 3-phenyl-4,5-dimethylthiazolium chloride (9a) (113.0 mg, 0.50 mmol, 1 equiv.), silver(I) oxide (58.0 mg, 0.025 mmol, 0.5 equiv.), and 4 Å molecular sieves (113 mg) were suspended in CH$_2$Cl$_2$ (7 mL) in the dark. The reaction mixture was stirred at room temperature for 1 h. Catalyst 10 (270 mg, 0.45 mmol, 0.9 equiv.) was added as a solid in one portion, the reaction flask was taken out of the glove box and stirred under a nitrogen atmosphere at room temperature for 1.5 h in the dark. The solvent was removed in vacuo, the remaining solid was dissolved in a minimum amount of C$_6$H$_6$, and poured onto a column packed with TSI Scientific silica gel. The complex was eluted with pentanes/diethyl ether (1/1) as a brown-green band. This was concentrated in vacuo, transferred in a glove box, dissolved in the minimum amount of benzene and lyophilized to afford the desired complex as a brown-yellow solid (75 mg, 0.147 mmol, 32% yield). The solid is stable in air in the solid state and soluble in CH$_2$Cl$_2$, CHCl$_3$, benzene, toluene and THF. $^1$H NMR (CD$_2$Cl$_2$. 500 MHz): δ=17.93 (s, 1H), 7.90-7.88 (m, 2H), 7.79-7.77 (m, 1H), 7.70-7.58 (m, 4H), 7.15-7.08 (m, 2H), 5.14 (septet, J=6 Hz, 1H), 2.42 (s, 3H), 2.12 (s, 3H), 1.52 (d, J=6 Hz, 6H); $^{13}$C{$^1$H} NMR (CD$_2$Cl$_2$, 125 MHz): δ=287.26, 215.05, 154.90, 143.80, 142.49, 139.96, 130.36, 129.71, 129.57, 129.18, 122.95, 122.26, 113.68, 75.67, 21.72, 12.97, 12.71.

The crystal structure of catalyst 1 is shown in FIG. 1, which is confirmed by the X-ray crystallography results, set forth in Table 1, below:

TABLE 1

| Data supporting crystal structure of Catalyst 1 ||
|---|---|
| Empirical formula | C$_{21}$H$_{23}$NOSCl$_2$Ru |
| Formula weight | 509.43 |
| Crystallization Solvent | Hexanes/deuterated benzene |
| Crystal Habit | Plate |
| Crystal size | 0.44 × 0.36 × 0.11 mm$^3$ |
| Crystal color | Brown |
| Data Collection ||
| Type of diffractometer | Bruker SMART 1000 |
| Wavelength | 0.71073 Å MoKα |
| Data Collection Temperature | 100(2) K |
| θ range for 27295 reflections used in lattice determination | 2.54 to 46.26° |
| Unit cell dimensions | a = 8.6637(3) Å |
|  | b = 23.1580(7) Å β = 99.6310(10)° |
|  | c = 10.7183(3) Å |
| Volume | 2120.15(11) Å$^3$ |
| Z | 4 |
| Crystal system | Monoclinic |
| Space group | P2$_1$/n |
| Density (calculated) | 1.596 Mg/m$^3$ |
| F(000) | 1032 |
| Data collection program | Bruker SMART v5.630 |
| θ range for data collection | 1.76 to 46.38° |
| Completeness to θ = 46.38° | 93.5% |
| Index ranges | −17 ≤ h ≤ 15, −36 ≤ k ≤ 47, −21 ≤ l ≤ 21 |
| Data collection scan type | ω scans at 7 φ settings |
| Data reduction program | Bruker SAINT v6.45A |
| Reflections collected | 66368 |
| Independent reflections | 17553 [R$_{int}$ = 0.0916] |
| Absorption coefficient | 1.101 mm$^{-1}$ |

TABLE 1-continued

Data supporting crystal structure of Catalyst 1

| | |
|---|---|
| Absorption correction | None |
| Max. and min. transmission | 0.8885 and 0.6430 |
| Structure solution and Refinement | |
| Structure solution program | Bruker XS v6.12 |
| Primary solution method | Direct methods |
| Secondary solution method | Difference Fourier map |
| Hydrogen placement | Difference Fourier map |
| Structure refinement program | Bruker XL v6.12 |
| Refinement method | Full matrix least-squares on $F^2$ |
| Data/restraints/parameters | 7553/0/336 |
| Treatment of hydrogen atoms | Unrestrained |
| Goodness-of-fit on $F^2$ | 1.278 |
| Final R indices [I > 2σ(I), 12405 reflections] | R1 = 0.0432, wR2 = 0.0799 |
| R indices (all data) | R1 = 0.0685, wR2 = 0.0832 |
| Type of weighting scheme used | Sigma |
| Weighting scheme used | $w = 1/\sigma^2(Fo^2)$ |
| Max shift/error | 0.001 |
| Average shift/error | 0.000 |
| Largest diff. peak and hole | 3.779 and −1.566 e · Å$^{-3}$ |

Example 2(b)

Preparation of [RuCl$_2$ (3-(2-methylphenyl)-4,5-dimethylthiazol-2-ylidene) (=CH-o-iPrO-Ph)] Catalyst 2

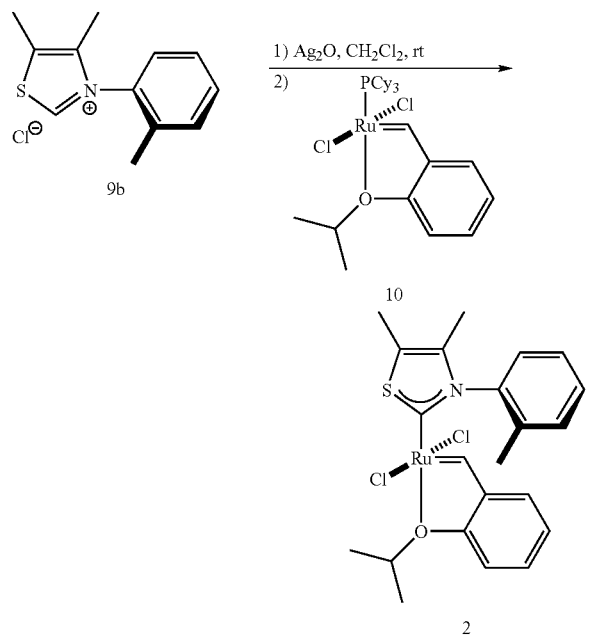

In a glove box, 3-(2-methylphenyl)-4,5-dimethylthiazolium chloride (9b) (120.0 mg, 0.50 mmol, 1 equiv.), silver(I) oxide (58.0 mg, 0.025 mmol, 0.5 equiv.), and 4 Å molecular sieves (113 mg) were suspended in CH$_2$Cl$_2$ (7 mL) in the dark. The reaction mixture was stirred at room temperature for 1 h. Catalyst 10 (270 mg, 0.45 mmol, 0.9 equiv.) was added as a solid in one portion, the reaction flask was taken out of the glove box and stirred under a nitrogen atmosphere at room temperature for 1.5 h in the dark. The solvent was removed in vacuo, the remaining solid was dissolved in a minimum amount of C$_6$H$_6$, and poured onto a column packed with TSI Scientific silica gel. The complex was eluted with pentanes/diethyl ether (1/1) as a brown band. This was concentrated in vacuo, transferred in a glove box, dissolved in the minimum amount of benzene and lyophilized to afford the desired complex as a brown solid (125 mg, 0.239 mmol, 53% yield). The solid is stable in air in the solid state and soluble in CH$_2$Cl$_2$, CHCl$_3$, benzene, toluene and THF. $^1$H NMR (CD$_2$Cl$_2$, 500 MHz): δ=17.92 (s, 1H), 8.09-8.07 (m, 1H), 7.79-7.77 (m, 1H), 7.70-7.67 (m, 1H), 7.53-7.49 (m, 2H), 7.44-7.42 (m, 1H), 7.15-7.07 (m, 2H), 5.12 (septet, J=6 Hz, 1H), 2.42 (s, 3H), 2.16 (s, 3H), 2.01 (s, 3H), 1.53 (d, J=6 Hz, 3H), 1.44 (d, J=6 Hz, 3H); $^{13}$C{$^1$H} NMR (CD$_2$Cl$_2$, 125 MHz): δ=287.59, 215.39, 155.23, 144.13, 142.82, 140.29, 130.70, 130.04, 129.90, 129.52, 123.29, 122.59, 114.02, 76.01, 22.06, 13.31, 13.05.

Figure 2:
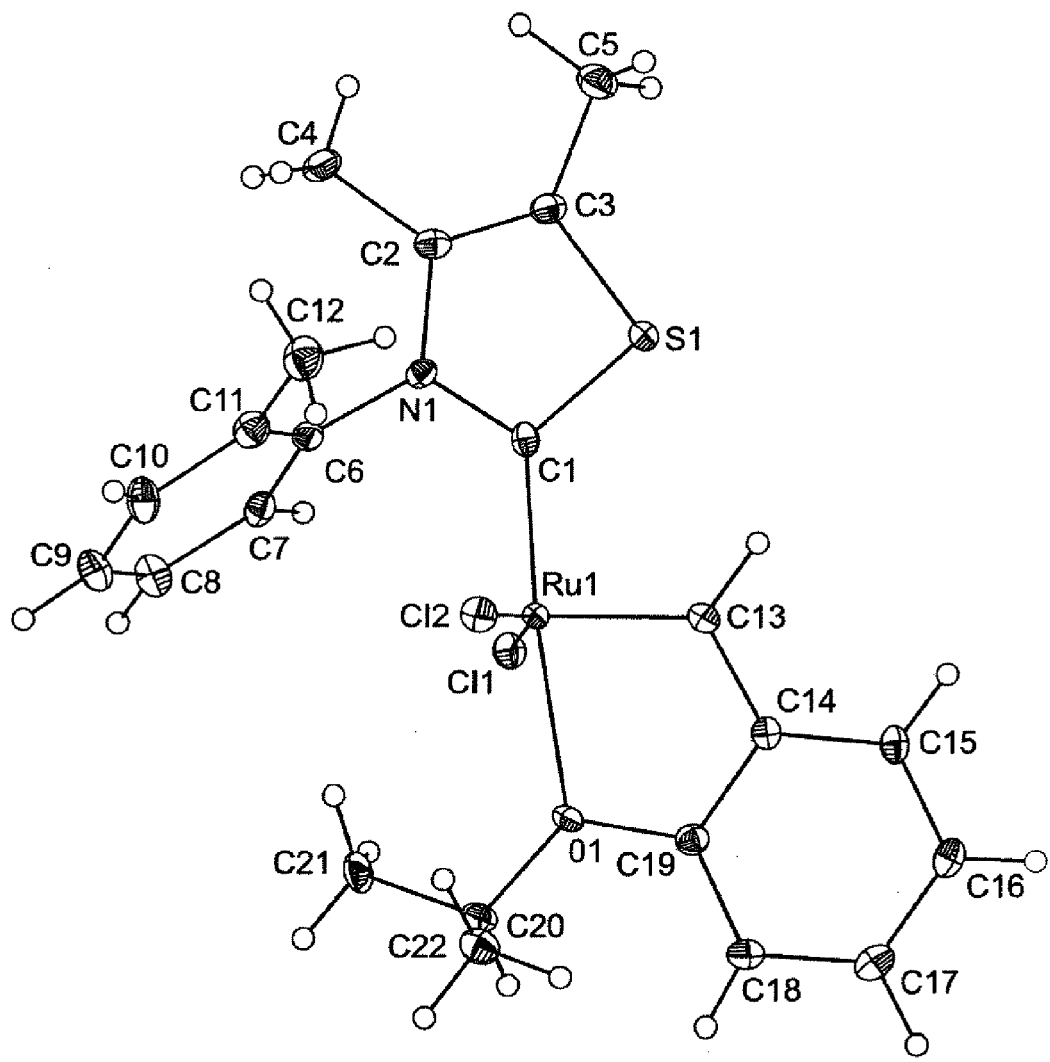
FIG. 2 depicts the crystal structure of catalyst 2.

The crystal structure of catalyst 2 is shown in FIG. 2, which is confirmed by the X-ray crystallography results, set forth in Table 2, below:

TABLE 2

Data supporting crystal structure of Catalyst 2

| | |
|---|---|
| Empirical formula | C$_{22}$H$_{25}$NOSCl$_2$Ru |
| Formula weight | 523.46 |
| Crystallization Solvent | Hexanes/deuterated benzene |
| Crystal Habit | Triangular |
| Crystal size | 0.27 × 0.23 × 0.18 mm$^3$ |
| Crystal color | Brown |

TABLE 2-continued

Data supporting crystal structure of Catalyst 2

Data Collection

| | |
|---|---|
| Type of diffractometer | Bruker SMART 1000 |
| Wavelength | 0.71073 Å MoKα |
| Data Collection Temperature | 100(2) K |
| θ range for 17769 reflections used in lattice determination | 2.32 to 39.90° |
| Unit cell dimensions | a = 9.7492(3) Å |
| | b = 11.2812(4) Å |
| | c = 20.1232(6) Å |
| Volume | 2213.20(12) Å$^3$ |
| Z | 4 |
| Crystal system | Orthorhombic |
| Space group | P2$_1$2$_1$2$_1$ |
| Density (calculated) | 1.571 Mg/m$^3$ |
| F(000) | 1064 |
| Data collection program | Bruker SMART v5.630 |
| θ range for data collection | 2.02 to 40.55° |
| Completeness to θ = 40.55° | 94.8% |
| Index ranges | −17 ≦ h ≦ 15, −20 ≦ k ≦ 15, −36 ≦ l ≦ 36 |
| Data collection scan type | ω scans at 5 φ settings |
| Data reduction program | Bruker SAINT v6.45A |
| Reflections collected | 48121 |
| Independent reflections | 12769 [R$_{int}$ = 0.0912] |
| Absorption coefficient | 1.057 mm$^{-1}$ |
| Absorption correction | None |
| Max. and min. transmission | 0.8325 and 0.7634 |

Structure solution and Refinement

| | |
|---|---|
| Structure solution program | Bruker XS v6.12 |
| Primary solution method | Direct methods |
| Secondary solution method | Difference Fourier map |
| Hydrogen placement | Difference Fourier map |
| Structure refinement program | Bruker XL v6.12 |
| Refinement method | Full matrix least-squares on F$^2$ |
| Data/restraints/parameters | 12769/0/353 |
| Treatment of hydrogen atoms | Unrestrained |
| Goodness-of-fit on F$^2$ | 1.079 |
| Final R indices [I > 2σ(I), 9250 reflections] | R1 = 0.0426, wR2 = 0.0669 |
| R indices (all data) | R1 = 0.0668, wR2 = 0.0707 |
| Type of weighting scheme used | Sigma |
| Weighting scheme used | w = 1/σ$^2$(Fo$^2$) |
| Max shift/error | 0.002 |
| Average shift/error | 0.000 |
| Absolute structure determination | Anomalous differences |
| Absolute structure parameter | −0.03(2) |
| Largest diff. peak and hole | 1.424 and −1.930 e · Å$^{-3}$ |

Example 2(c)

Preparation of [RuCl$_2$ (3-(2,4,6-trimethylphenyl)-4,5-dimethylthiazol-2-ylidene) (═CH-o-iPrO-Ph)] Catalyst 3

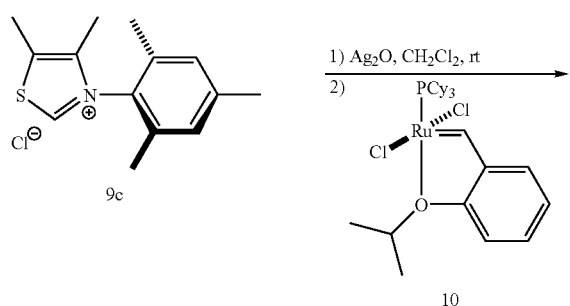

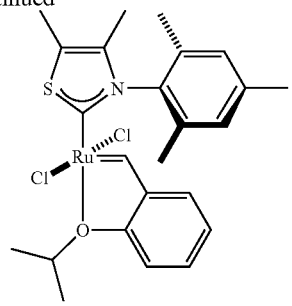

2

In a glove box, 3-(2,4,6-trimethylphenyl)-4,5-dimethylthiazolium chloride (9c) (93.8 mg, 0.35 mmol, 1 equiv.), silver (I) oxide (40.6 mg, 0.175 mmol, 0.5 equiv.), and 4 Å molecular sieves (95 mg) were suspended in CH$_2$Cl$_2$ (5 mL) in the dark. The reaction mixture was stirred at room temperature for 1 h. Catalyst 10 (189 mg, 0.315 mmol, 0.9 equiv.) was added as a solid in one portion, the reaction flask was taken out of the glove box and stirred under a nitrogen atmosphere at room temperature for 1 h in the dark. The solvent was removed in vacuo, the remaining solid was dissolved in a minimum amount of $C_6H_6$, and poured onto a column packed with TSI Scientific silica gel. The complex was eluted with pentanes/diethyl ether (1/1) as a brown band. This was concentrated in vacuo, transferred in a glove box, dissolved in the minimum amount of benzene and lyophilized to afford the desired complex as a brown solid (93 mg, 0.168 mmol, 54% yield). The solid is stable in air in the solid state and soluble in $CH_2Cl_2$, $CHCl_3$, benzene, toluene and THF. Crystals suitable for X-ray crystallography were grown at room temperature by slow diffusion of hexanes into a solution of 3 in benzene. $^1$H NMR ($CD_2Cl_2$, 500 MHz): δ=17.27 (s, 1H), 7.67-7.59 (m, 2H), 7.12-7.07 (m, 4H), 5.17 (septet, J=6 Hz, 1H), 2.43 (s, 6H), 2.09 (s, 6H), 1.87 (s, 3H), 1.61 (d, J=6 Hz, 6H); $^{13}$C{$^1$H} NMR ($CD_2Cl_2$, 125 MHz): δ 284.03, 211.33, 154.36, 143.92, 140.58, 139.78, 138.08, 137.00, 130.82, 130.10, 129.31, 122.81, 122.43, 113.62, 75.93, 21.74, 21.19, 18.71, 12.69, 11.90; FIRMS (FAB$^+$) calculated for $C_{24}H_{329}Cl_2NORuS$ [M]$^+$ 551.0391, observed 551.0382.

Figure 3A:
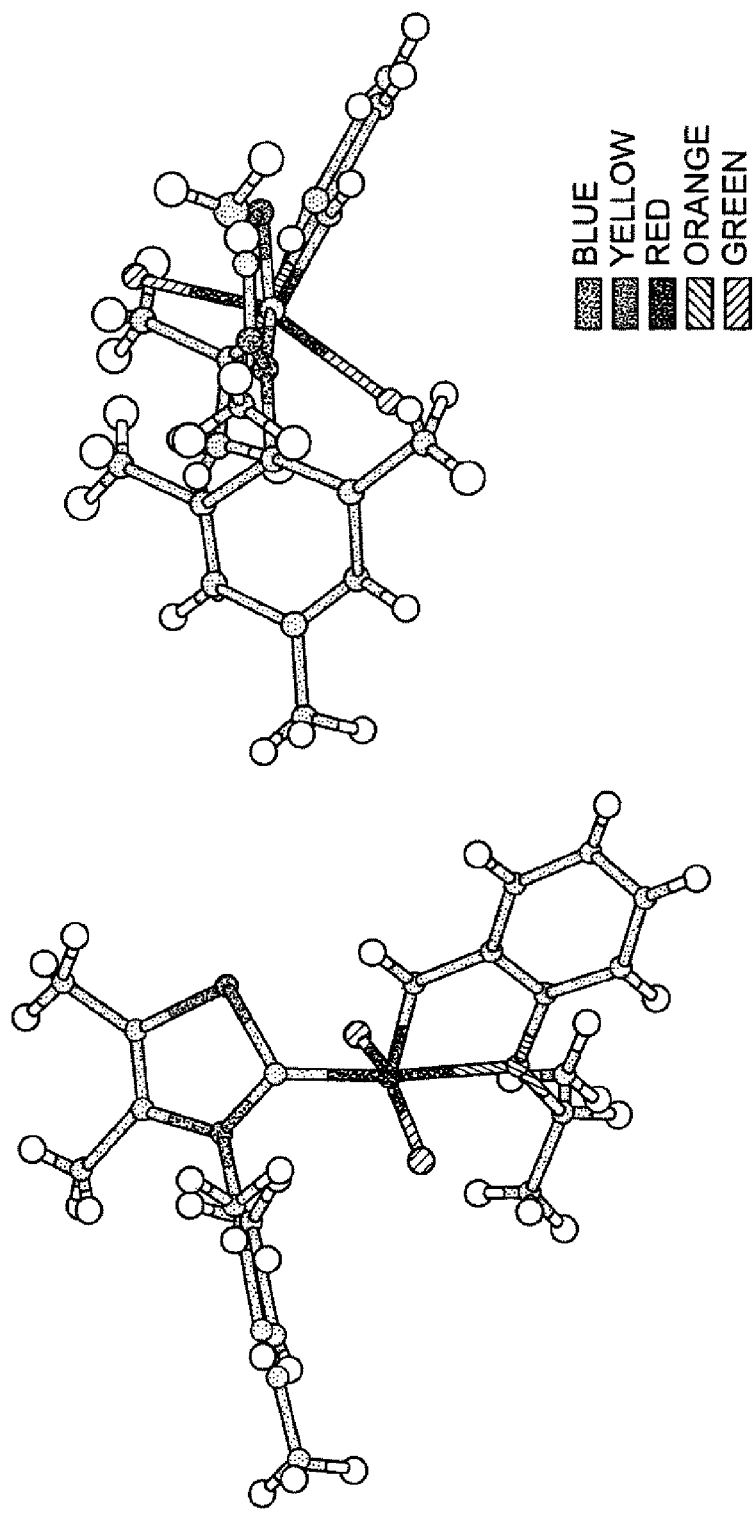
Figure 3B:
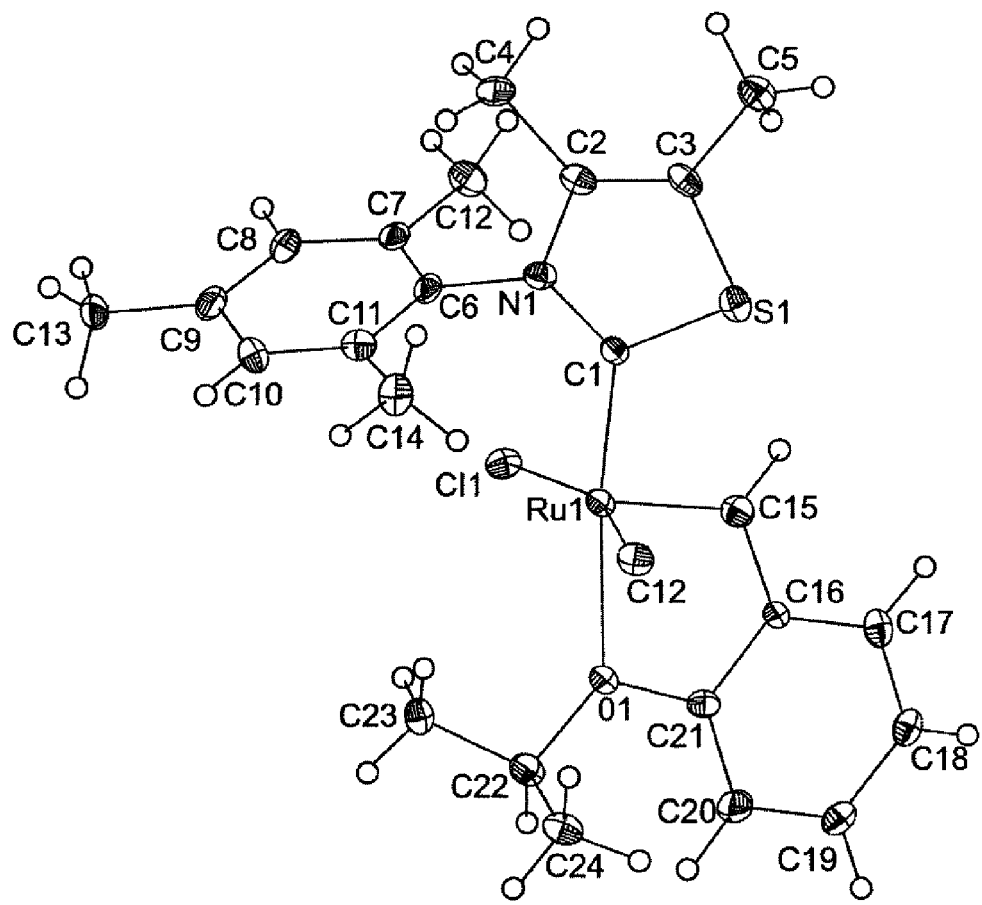

The crystal structure of catalyst 3 is shown in FIGS. 3(*a*), 3(*b*), and 3(*c*), which is confirmed by the X-ray crystallography results, set forth in Table 3, below:

TABLE 3

| Data supporting crystal structure of Catalyst 3 | |
|---|---|
| Empirical formula | $C_{24}H_{29}NOSCl_2Ru•½(C_6H_6)$ |
| Formula weight | 590.57 |
| Crystallization Solvent | Benzene/hexanes |
| Crystal Habit | Fragment |
| Crystal size | 0.35 × 0.27 × 0.19 mm$^3$ |
| Crystal color | Dark green |
| Data Collection | |
| Type of diffractometer | Bruker SMART 1000 |
| Wavelength | 0.71073 Å MoKα |
| Data Collection Temperature | 100(2) K |
| θ range for 28680 reflections used in lattice determination | 2.29 to 41.72° |
| Unit cell dimensions | a = 12.5506(4) Å |
| | b = 15.6147(4) Å β = 109.0050(10)° |
| | c = 14.3088(4) Å |
| Volume | 2651.30(13) Å$^3$ |
| Z | 4 |
| Crystal system | Monoclinic |
| Space group | P2$_1$/n |
| Density (calculated) | 1.480 Mg/m$^3$ |
| F(000) | 1212 |
| Data collection program | Bruker SMART v5.630 |
| θ range for data collection | 1.88 to 41.85° |
| Completeness to θ = 41.85° | 96.0% |
| Index ranges | −23 ≤ h ≤ 21, −29 ≤ k ≤ 28, −26 ≤ l ≤ 26 |
| Data collection scan type | ω scans at 7 φ settings |
| Data reduction program | Bruker SAINT v6.45A |
| Reflections collected | 73622 |
| Independent reflections | 17644 [R$_{int}$ = 0.0800] |
| Absorption coefficient | 0.892 mm$^{-1}$ |
| Absorption correction | None |
| Max. and min. transmission | 0.8488 and 0.7455 |
| Structure solution and Refinement | |
| Structure solution program | Bruker XS v6.12 |
| Primary solution method | Direct methods |
| Secondary solution method | Difference Fourier map |
| Hydrogen placement | Geometric positions |
| Structure refinement program | Bruker XL v6.12 |
| Refinement method | Full matrix least-squares on F$^2$ |
| Data/restraints/parameters | 17644/0/305 |
| Treatment of hydrogen atoms | Riding |
| Goodness-of-fit on F$^2$ | 1.217 |
| Final R indices [I > 2σ(I), 12744 reflections] | R1 = 0.0350, wR2 = 0.0674 |
| R indices (all data) | R1 = 0.0563, wR2 = 0.0706 |
| Type of weighting scheme used | Sigma |
| Weighting scheme used | w = 1/σ$^2$(Fo$^2$) |
| Max shift/error | 0.001 |
| Average shift/error | 0.000 |
| Largest diff. peak and hole | 1.489 and −1.084 e · Å$^{-3}$ |

Example 2(d)

Preparation of [RuCl$_2$ (3-(2,6-diethylphenyl)-4,5-dimethylthiazol-2-ylidene) (=CH-o-iPrO-Ph)] Catalyst 4

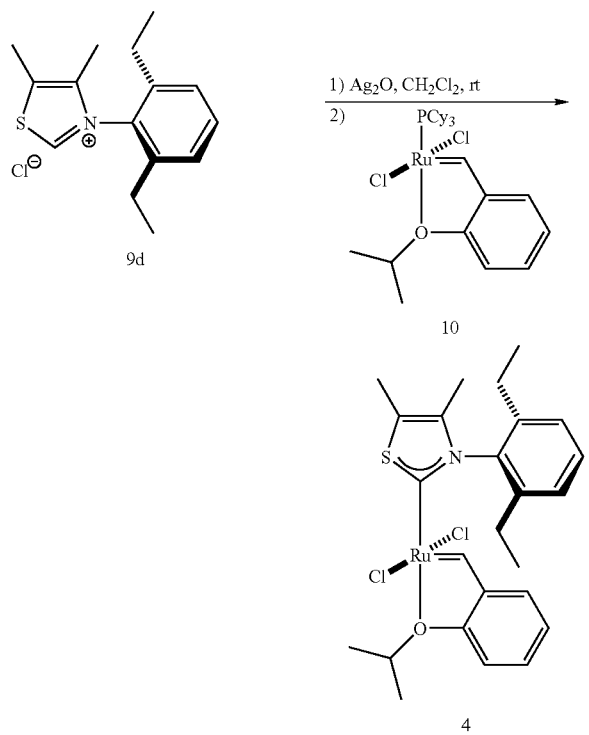

In a glove box, 3-(2,6-diethylphenyl)-4,5-dimethylthiazolium chloride (9d) (70.5 mg, 0.25 mmol, 1 equiv.), silver(I) oxide (29.0 mg, 0.125 mmol, 0.5 equiv.), and 4 Å molecular sieves (71 mg) were suspended in CH$_2$Cl$_2$ (3.5 mL) in the dark. The reaction mixture was stirred at room temperature for 1 h. Catalyst 10 (135 mg, 0.225 mmol, 0.9 equiv.) was added as a solid in one portion, the reaction flask was taken out of the glove box and stirred under a nitrogen atmosphere at room temperature for 16 h in the dark. The solvent was removed in vacuo, the remaining solid was dissolved in a minimum amount of C$_6$H$_6$, and poured onto a column packed with TSI Scientific silica gel. The complex was eluted with pentanes/diethyl ether (1/1) as a brown band. This was concentrated in vacuo, transferred in a glove box, dissolved in the minimum amount of benzene and lyophilized to afford the desired complex as a brown solid (74 mg, 0.131 mmol, 58% yield). The solid is stable in air in the solid state and soluble in CH$_2$Cl$_2$, CHCl$_3$, benzene, toluene and THF. Crystals suitable for X-ray crystallography were grown at room temperature by slow diffusion of hexanes into a solution of 4 in benzene. $^1$H NMR (CD$_2$Cl$_2$, 500 MHz): δ=17.27 (s, 1H), 7.66-7.62 (m, 2H), 7.54 (t, J=8 Hz, 1H), 7.34 (d, J=8 Hz, 2H), 7.11-7.06 (m, 2H), 5.16 (septet, J=6 Hz, 1H), 2.62 (m, 2H), 2.43 (s, 3H), 2.24 (m, 2H), 1.88 (s, 3H), 1.59 (d, J=6 Hz, 6H), 1.17 (t, J=7 Hz, 61-1) $^{13}$C{$^1$H} NMR (CD$_2$Cl$_2$, 125 MHz): δ=282.90, 210.53, 154.52, 143.77, 142.20, 140.93, 139.54, 131.26, 130.09, 130.00, 125.80, 122.79, 122.42, 113.65, 75.91, 31.52, 27.39, 27.30, 26.08, 24.06, 21.76, 13.23, 12.71, 12.28; HRMS (FAB) calculated for C$_{25}$H$_{30}$Cl$_2$NORuS [M]$^+$ 564.0469, observed 564.0461.

Figure 4B:
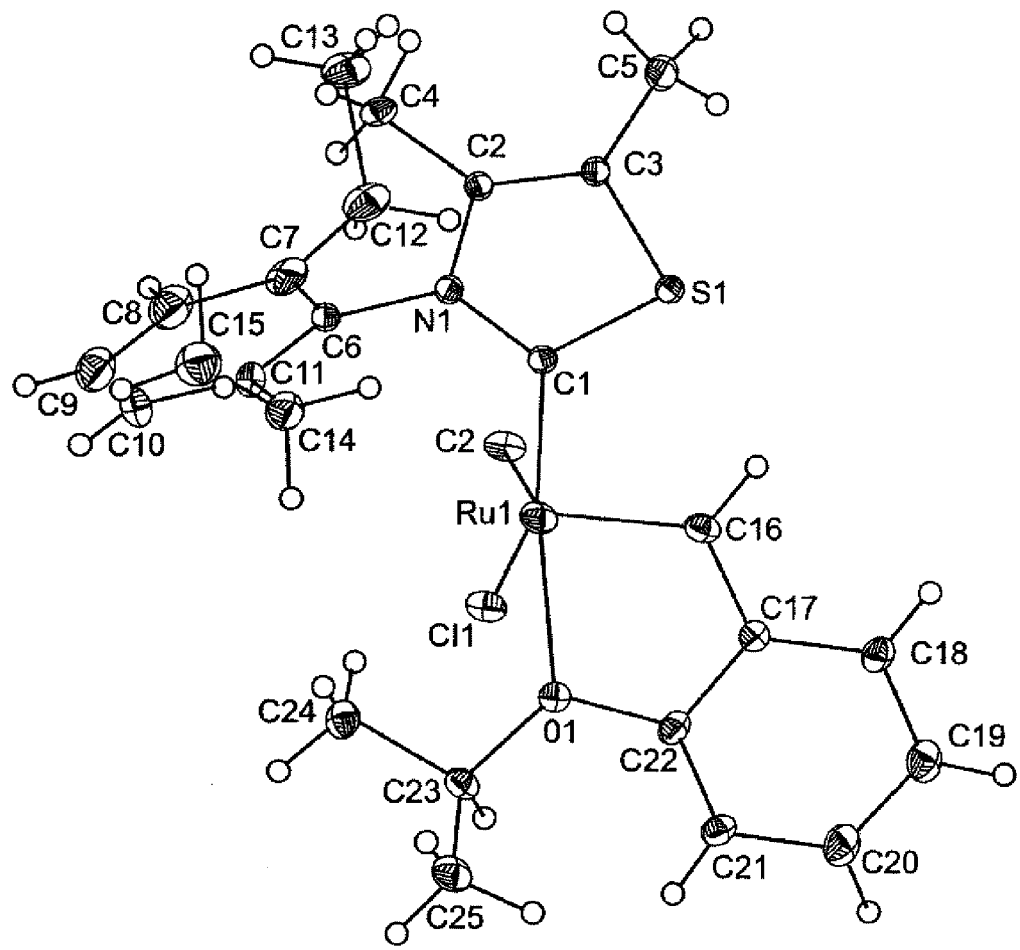
Figure 5:
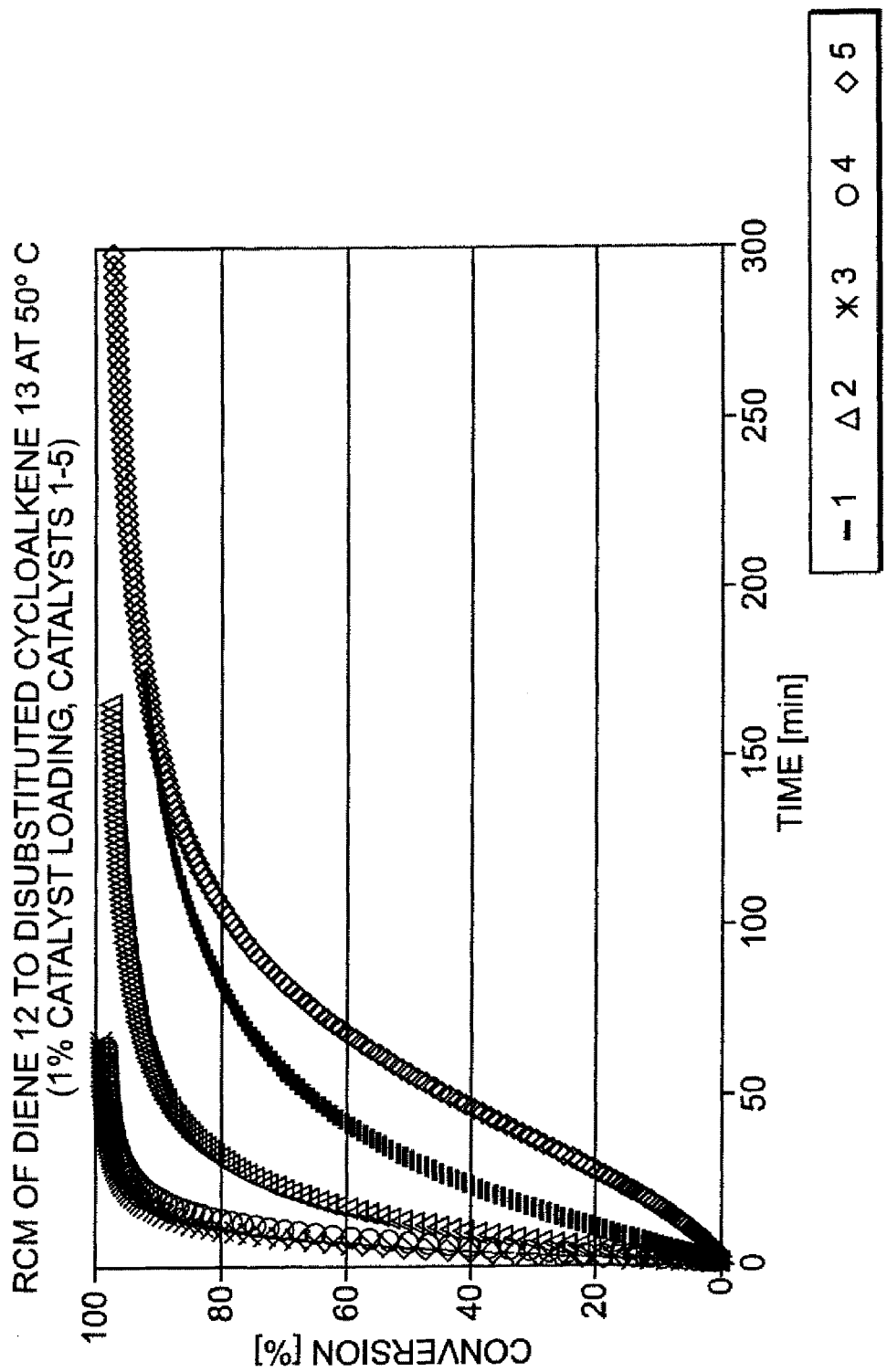
FIG. 5 shows the results of a ring-closing metathesis reaction of a diethyldiallyl malonate to a disubstituted cycloalkene at 50° C. (1% catalyst loading) using catalysts 1-5.
Figure 6:
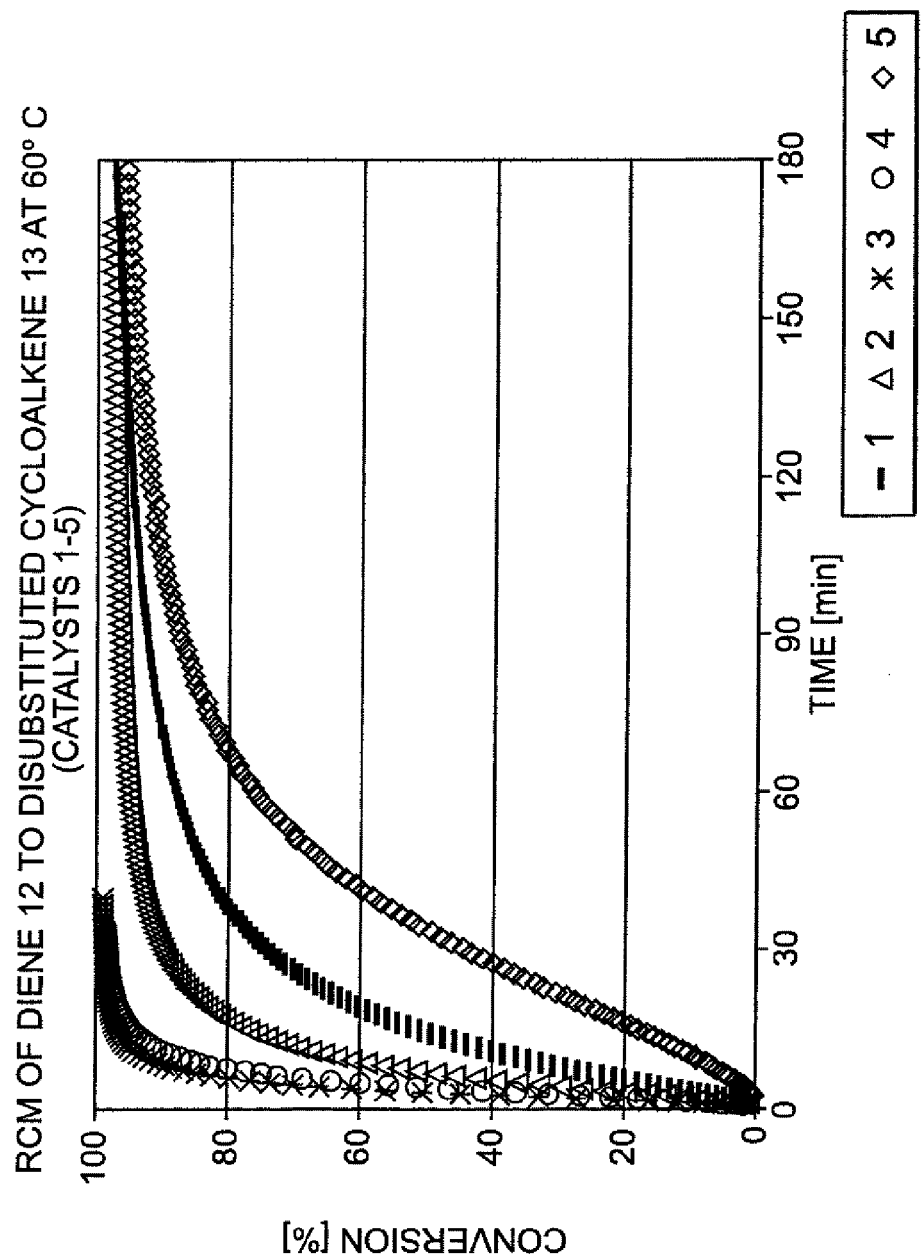
FIG. 6 shows the results of a ring-closing metathesis reaction of diethyldiallyl malonate to a disubstituted cycloalkene at 60° C. (1% catalyst loading) using catalysts 1-5.
Figure 7:
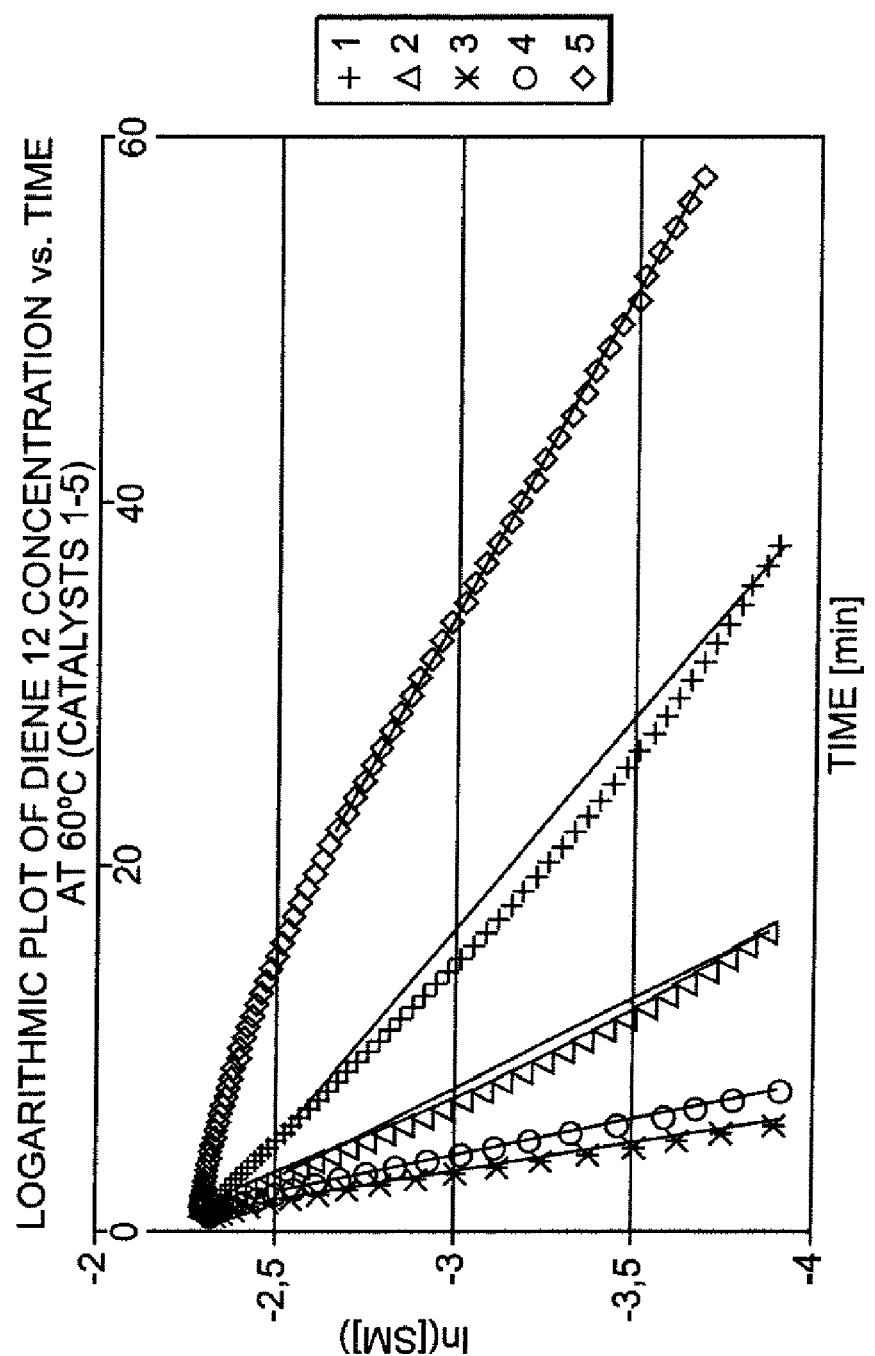
FIG. 7 depicts a logarithmic plot of diethyldiallyl malonate concentration plotted against time in a ring-closing metathesis reaction converting the diethyldiallyl malonate to a disubstituted cycloalkene at 60° C. (1% catalyst loading) using catalysts 1-5.
Figure 8:
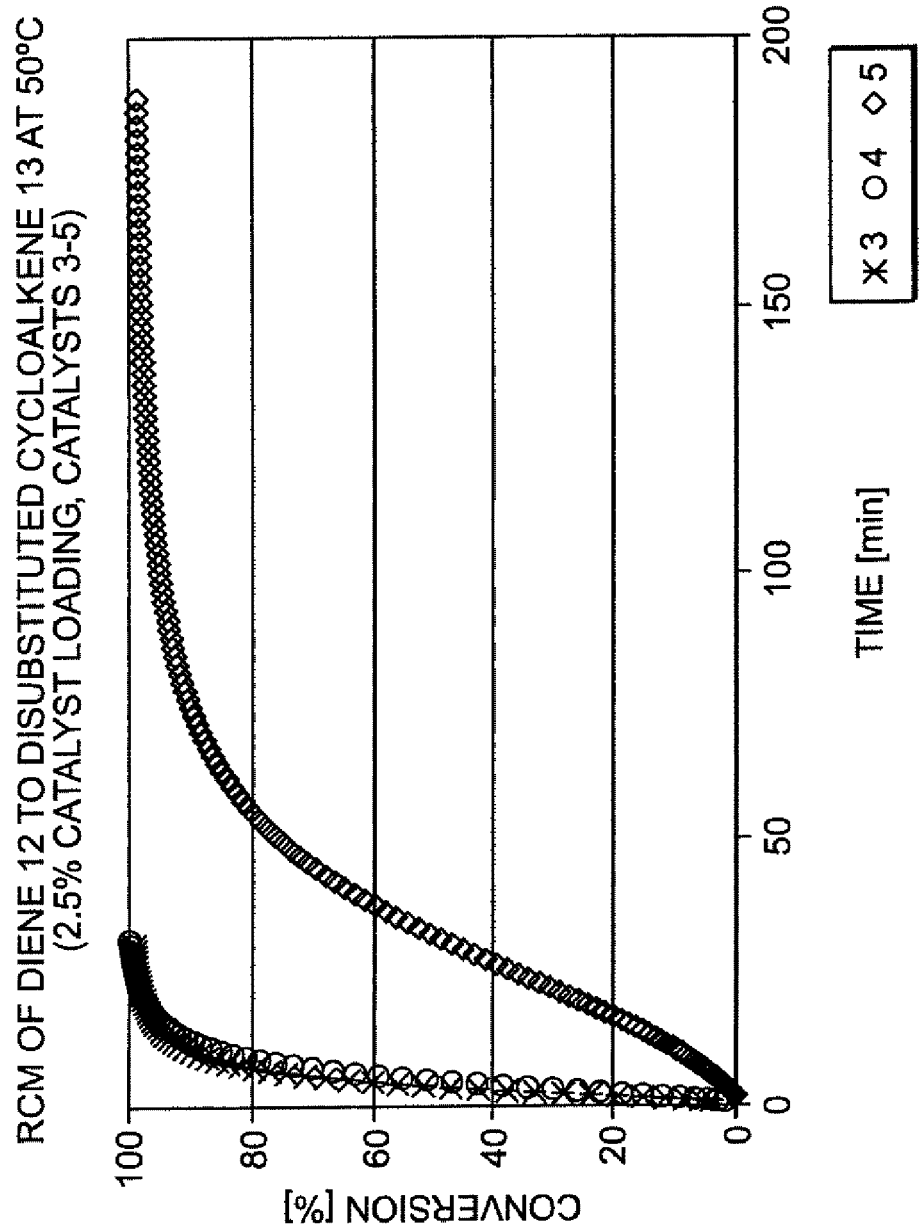
FIG. 8 shows the results of a ring-closing metathesis reaction of diethyldiallyl malonate to a disubstituted cycloalkene at 50° C. (2.5% catalyst loading) using catalysts 3-5.

The crystal structure of catalyst 4 is shown in FIGS. 4(*a*) and 4(*b*), which is confirmed by the X-ray crystallography results, set forth in Table 4, below:

TABLE 4

| Data supporting structure of catalyst 4 | |
|---|---|
| Empirical formula | C$_{25}$H$_{31}$NOSCl$_2$Ru |
| Formula weight | 565.54 |
| Crystallization Solvent | Not given |
| Crystal Habit | Fragment |
| Crystal size | 0.34 × 0.31 × 0.29 mm$^3$ |
| Crystal color | Green/brown |
| Data Collection | |
| Type of diffractometer | Bruker SMART 1000 |
| Wavelength | 0.71073 Å MoKα |
| Data Collection Temperature | 100(2) K |
| θ range for 33391 reflections used in lattice determination | 2.49 to 42.63° |
| Unit cell dimensions | a = 16.2291(4) Å |
| | b = 9.3934(2) Å β = 99.5100(10)° |
| | c = 16.6087(4) Å |
| Volume | 2497.14(10) Å$^3$ |
| Z | 4 |
| Crystal system | Monoclinic |
| Space group | P2$_1$/c |
| Density (calculated) | 1.504 Mg/m$^3$ |
| F(000) | 1160 |
| Data collection program | Bruker SMART v5.630 |
| θ range for data collection | 2.49 to 42.83° |
| Completeness to θ = 42.83° | 94.3% |
| Index ranges | −30 ≤ h ≤ 30, −17 ≤ k ≤ 17, −31 ≤ l ≤ 28 |
| Data collection scan type | ω scans at 7 φ settings |
| Data reduction program | Bruker SAINT v6.45A |
| Reflections collected | 69940 |
| Independent reflections | 17254 [R$_{int}$ = 0.0794] |

TABLE 4-continued

| Data supporting structure of catalyst 4 | |
|---|---|
| Absorption coefficient | 0.943 mm$^{-1}$ |
| Absorption correction | None |
| Max. and min. transmission | 0.7716 and 0.7399 |
| Structure solution and Refinement | |
| Structure solution program | Bruker XS v6.12 |
| Primary solution method | Direct methods |
| Secondary solution method | Difference Fourier map |
| Hydrogen placement | Difference Fourier map |
| Structure refinement program | Bruker XL v6.12 |
| Refinement method | Full matrix least-squares on F$^2$ |
| Data/restraints/parameters | 17254/0/404 |
| Treatment of hydrogen atoms | unrestrained |
| Goodness-of-fit on F$^2$ | 1.261 |
| Final R indices [I > 2σ(I), 13175 reflections] | R1 = 0.0334, wR2 = 0.0666 |
| R indices (all data) | R1 = 0.0486, wR2 = 0.0690 |
| Type of weighting scheme used | Sigma |
| Weighting scheme used | w = 1/σ$^2$(Fo$^2$) |
| Max shift/error | 0.004 |
| Average shift/error | 0.000 |
| Largest diff. peak and hole | 1.328 and −1.075 e · Å$^{-3}$ |

Example 2(e)

Preparation of [RuCl$_2$ (3-(2,6-diisopropylphenyl)-4,5-dimethylthiazol-2-ylidene) (=CH-o-iPrO-Ph)] Catalyst 5

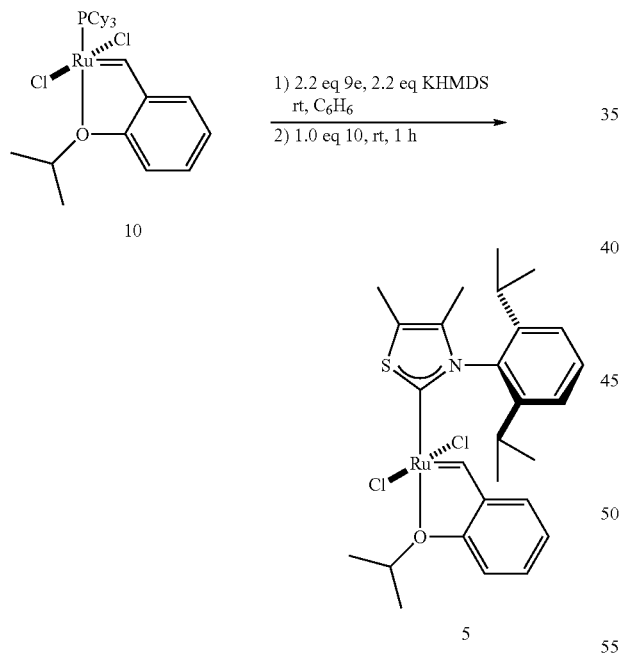

3-(2,6-diisopropylphenyl)-4,5-dimethylthiazolium chloride (9e) (190.8 mg, 0.616 mmol, 2.2 equiv.) was stirred with an equimolar quantity of KHMDS (122.8 mg, 0.616 mmol) in benzene (15 mL) in a glove box at room temperature for 30 min. Catalyst 10 (168.2 mg, 018 mmol, 1.0 equiv.) was added as a solid in one portion, the reaction flask was taken out of the glove box and stirred under a nitrogen atmosphere at room temperature for 1 h. The solution was concentrated to 2 mL in vacuo and poured onto a column packed with TSI Scientific silica gel. The complex was eluted with hexanes/diethyl ether (1/1) as a brown band. This was concentrated in vacuo, transferred in a glove box, dissolved in the minimum amount of benzene and lyophilized to afford the desired complex as a brown solid (66 mg, 0.11 mmol, 40% yield). The solid is stable in air in the solid state and soluble in CH$_2$Cl$_2$, CHCl$_3$, benzene, toluene and THF. Crystals suitable for X-ray crystallography were grown at room temperature by slow diffusion of hexanes into a solution of 5 in toluene. $^1$H NMR (CD$_2$Cl$_2$, 500 MHz): δ=16.60 (s, 1H), 7.63-7.57 (m, 2H), 7.38 (d, J=8 Hz, 2H), 7.07-7.02 (m, 3H), 5.19 (septet, J=6 Hz, 1H), 2.50 (septet, J=7 Hz, 2H), 2.42 (s, 3H), 1.91 (s, 1H), 1.70 (d, J=6 Hz, 6H), 1.12 (d, J=7 Hz, 6H), 1.03 (d. J=7 Hz, 6H); $^{13}$C{$^1$H} NMR (CD$_2$Cl$_2$, 125 MHz): 280.83 (d, J=52 Hz), 209.03, 162.87, 154.15, 147.58, 146.64, 143.30, 141.88, 138.53, 130.42, 129.81, 124.75, 122.63, 122.29, 113.50, 75.93, 28.41, 24.46, 24.12, 22.02, 12.99, 12.58; HRMS (FAB$^+$) calculated for C$_{27}$H$_{35}$NOCl$_2$RuS [M]$^+$ 593.0860, observed 593.0875. Anal. calculated for C$_{27}$H$_{35}$Cl$_2$NORuS: 54.63 C, 5.94H, 2.36 N. Found: 56.65 C, 5.72H, 2.70 N.

Example 2(f)

Preparation of [RuCl$_2$ (3-(2,4,6-trimethylphenyl)-4,5-dimethylthiazol-2-ylidene) (=CH-Ph) (PCy$_3$)] Catalyst 6

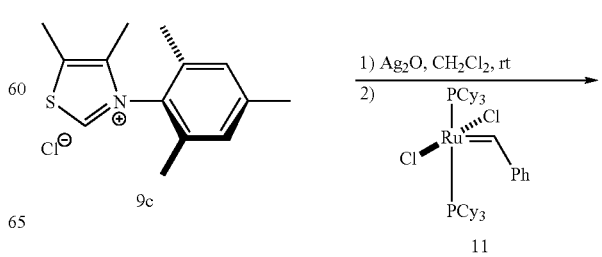

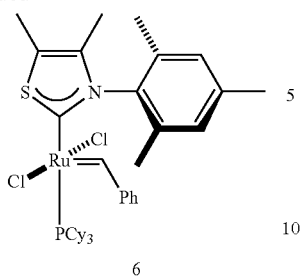

6

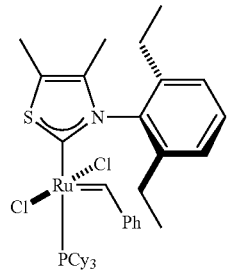

7

In a glove box, 3-(2,4,6-trimethylphenyl)-4,5-dimethylthiazolium chloride (9c) (134 mg, 0.5 mmol, 1 equiv.), silver(I) oxide (58 mg, 0.25 mmol, 0.5 equiv.), and 4 Å molecular sieves (135 mg) were suspended in $CH_2Cl_2$ (2.5 mL) in the dark. The reaction mixture was stirred at room temperature for 1 h. Catalyst 11 (370 mg, 0.45 mmol, 0.9 equiv.) was added as a solid in one portion, the reaction flask was taken out of the glove box and stirred under a nitrogen atmosphere at room temperature for 30 min in the dark. The solvent was removed in vacuo, the remaining solid was dissolved in a minimum amount of $C_6H_6$, and poured onto a column packed with TSI Scientific silica gel. The complex was eluted with diethyl ether/pentanes (15/85) as a green band. This was concentrated in vacuo, transferred in a glove box, dissolved in the minimum amount of benzene and lyophilized to afford the desired complex as a brown solid (105 mg, 0.136 mmol, 30% yield). The solid is stable in air in the solid state and soluble in $CH_2Cl_2$, $CHCl_3$, benzene, toluene and THF. $^1$H NMR ($CD_2Cl_2$, 500 MHz): δ=19.61 (d, J=6 Hz, 1H), 8.16 (d, J=8 Hz, 2H), 7.59 (t, J=8 Hz, 1H), 7.29 (t. J=8 Hz, 2H), 6.84 (s, 2H), 2.34-2.24 (m, 9H), 2.11 (s, 6H), 1.77 (s, 3H), 1.71-1.12 (m, 30H); $^{13}C\{^1H\}$ NMR ($CD_2Cl_2$, 125 MHz): δ=299.80, 220.39, 152.21, 140.31, 139.14, 137.94, 136.21, 131.24, 129.71, 129.46, 128.44, 32.53, 32.40, 29.96, 28.08, 28.00, 27.21, 26.66, 21.08, 18.88, 12.35, 11.67; HRMS (FAB$^+$) calculated for $C_{39}H_{56}Cl_2NPSRu$ [M]$^+$ 773.2292, observed 773.2316.

Example 2(g)

Preparation of [RuCl$_2$ (3-(2,6-diethylphenyl)-4,5-dimethylthiazol-2-ylidene) (=CH-Ph) (PCy$_3$)] Catalyst 7

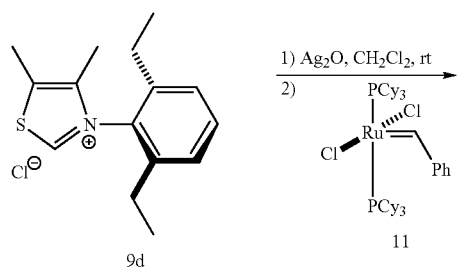

In a glove box, 3-(2,6-diethylphenyl)-4,5-dimethylthiazolium chloride (9d) (70.5 mg, 0.25 mmol, 1 equiv.), silver(I) oxide (29.0 mg, 0.125 mmol, 0.5 equiv.), and 4 Å molecular sieves (71 mg) were suspended in $CH_2Cl_2$ (3.5 mL) in the dark. The reaction mixture was stirred at room temperature for 1 h. Catalyst 11 (185 mg, 0.225 mmol, 0.9 equiv.) was added as a solid in one portion, the reaction flask was taken out of the glove box and stirred under a nitrogen atmosphere at room temperature for 1.5 h in the dark. The solvent was removed in vacuo, the remaining solid was dissolved in a minimum amount of $C_6H_6$, and poured onto a column packed with TSI Scientific silica gel. The complex was eluted with diethyl ether/pentanes (15/85) as a brown band. This was concentrated in vacuo, transferred in a glove box, dissolved in the minimum amount of benzene and lyophilized to afford the desired complex as a brown solid (72 mg, 0.091 mmol, 41% yield). The solid is stable in air in the solid state and soluble in $CH_2Cl_2$, $CHCl_3$, benzene, toluene and THF. $^1$H NMR ($CD_2Cl_2$, 500 MHz): δ=19.67 (d. J=7 Hz, 1H), 8.16-8.14 (m, 2H), 7.60 (t, J=7 Hz, 1H), 7.36-7.27 (m, 3H), 7.19-7.17 (m, 2H), 2.92 (m, 2H), 2.33-2.22 (m, 6H), 2.19-2.07 (m, 2H), 1.80 (s, 3H), 1.67-1.09 (m, 36H); $^{13}C\{^1H\}$ NMR ($CD_2Cl_2$, 125 MHz): δ=301.65, 219.36, 152.36, 141.37, 140.42, 140.39, 139.31, 131.28, 129.82, 129.78, 128.88, 128.52, 127.84, 126.65, 125.58, 32.53, 32.41, 31.16, 29.90, 28.08, 28.00, 27.63, 27.59, 26.65, 26.40, 24.19, 12.74, 12.35, 12.03; HRMS (FAB$^+$) calculated for $C_{40}H_{58}RuNPSCl_2$ [M]$^+$ 787.2449, observed 787.2460.

Example 3

Catalytic Activity of Catalysts 1-7

General procedure to prepare stock solutions: Two stock solutions can be prepared that contain enough catalyst for all the reactions. Inside a glovebox, a volumetric flask was charged with the catalyst (0.016 mmol) and $C_6D_6$ (or $CD_2Cl_2$) was added to prepare 1.0 mL of stock solution A (0.016 M). 0.5 ml of A was then transferred to another 2 ml volumetric flask and diluted to 2 ml with $C_6D_6$ (or $CD_2Cl_2$) to prepare stock solution B (0.004 M). This procedure was used to prepare stock solutions of catalysts 1-7 for the ring-closing metathesis (RCM), ring-opening metathesis polymerization (ROMP), and cross-metathesis (CM) standard activity tests.[4]

[4] All reactions were performed at least in duplicate to confirm reproducibility.

Figure 9:
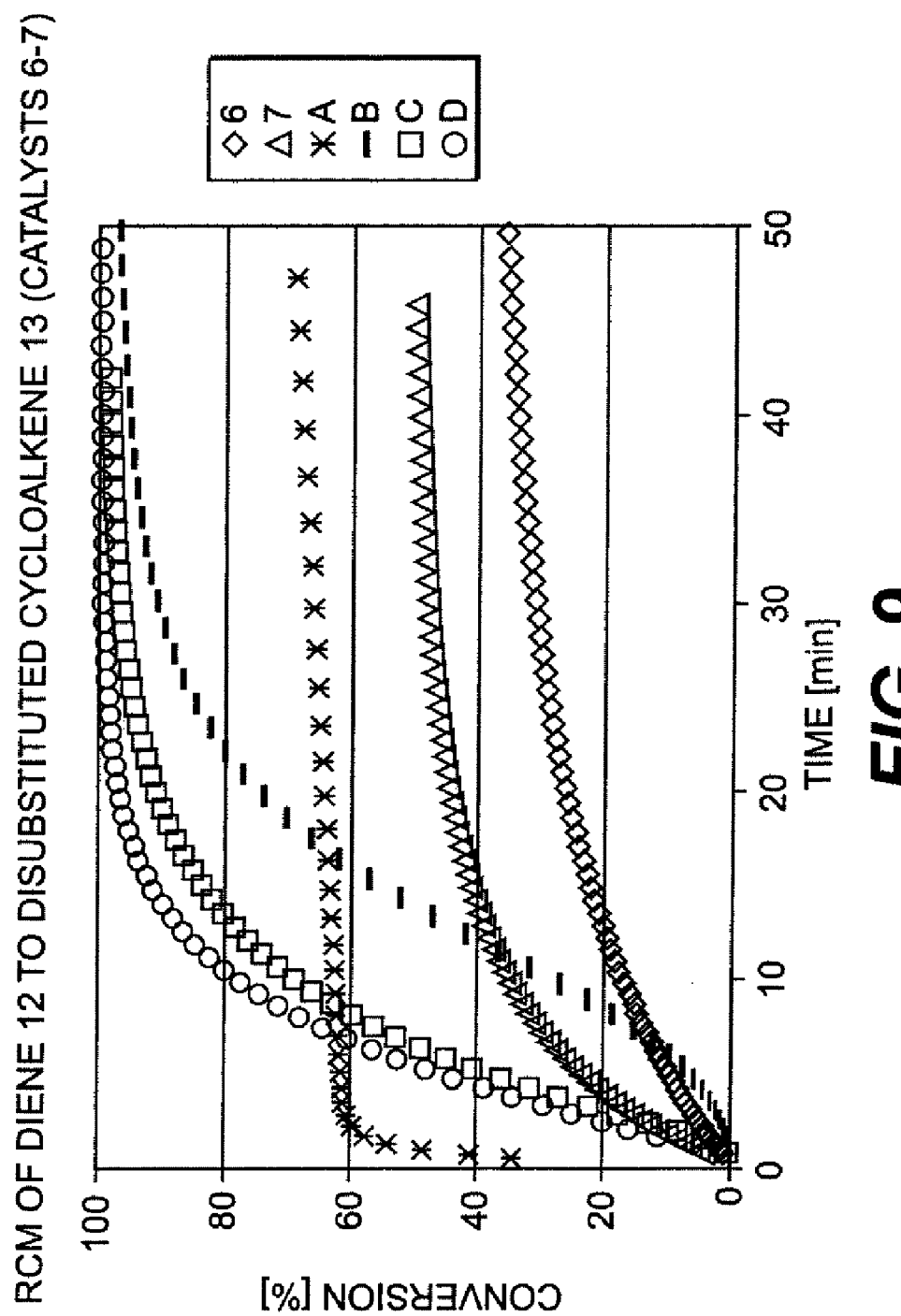
FIG. 9 shows the results of a ring-closing metathesis reaction of diethyldiallyl malonate to a disubstituted cycloalkene at 30° C. (1% catalyst loading) using catalysts 6-7.

In certain figures (FIGS. 9, 11, and 17-19), the catalysts of the invention are compared with conventional catalysts. The conventional catalysts are shown below: catalyst A (also referred to as a first-generation Grubbs catalyst); catalyst B (also referred to as a first-generation Hoveyda catalyst); catalyst C (also referred to as a second-generation Grubbs catalyst); and catalyst D (also referred to as a second-generation Hoveyda catalyst).

diallyl malonate (12) using catalysts 1-5, and FIG. 9 shows the results RCM of diethyldiallyl malonate (12) using catalysts 6-7.

Example 3(b)

RCM of Diethylallylmethallyl Malonate (14)

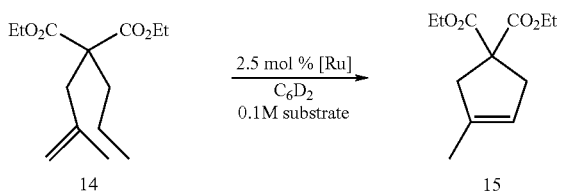

Figure 10:
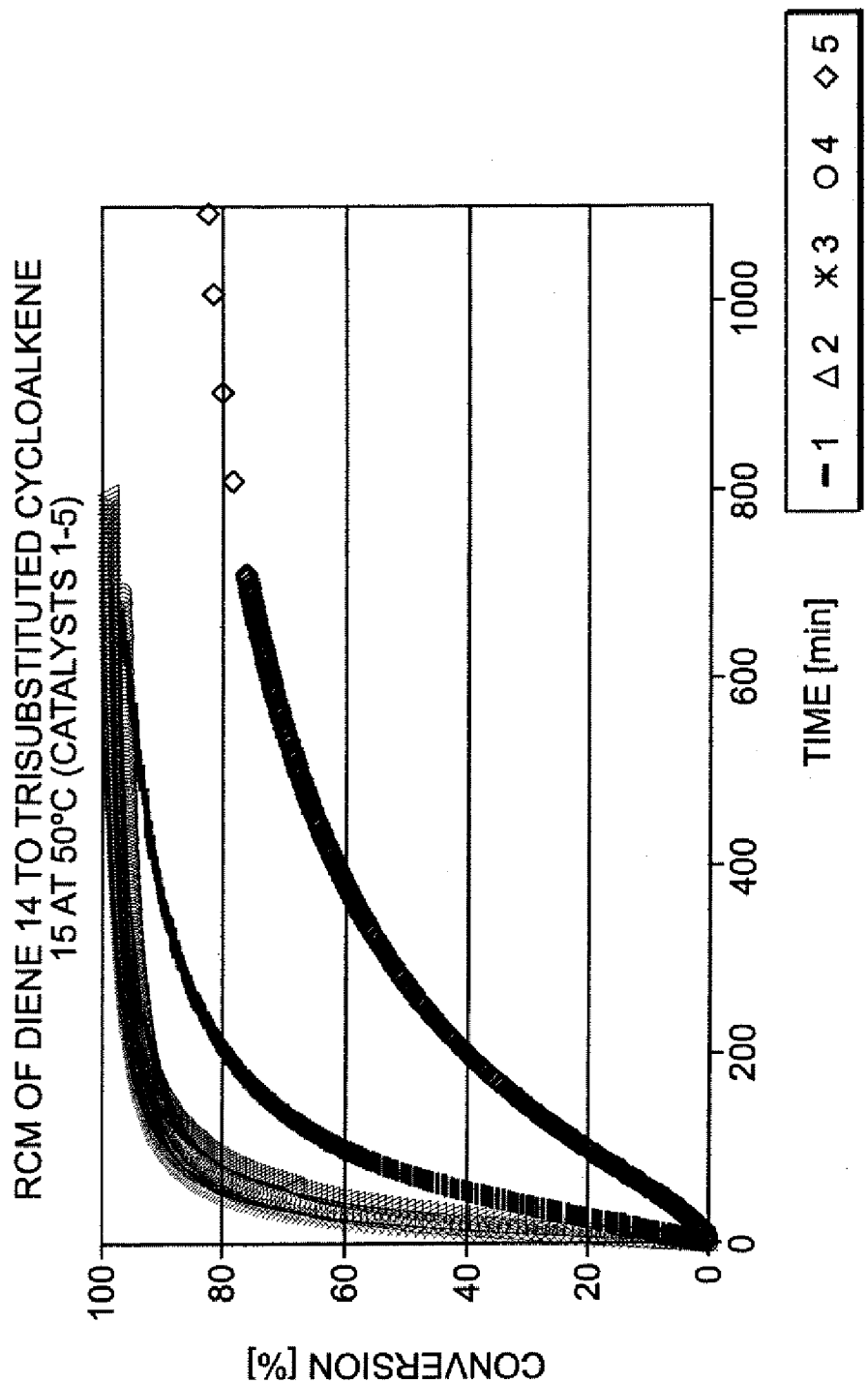
FIG. 10 shows the results of a ring-closing metathesis reaction of diethylallylmethallyl malonate to a trisubstituted cycloalkene at 50° C. (2.5% catalyst loading) using catalysts 1-5.
Figure 11:
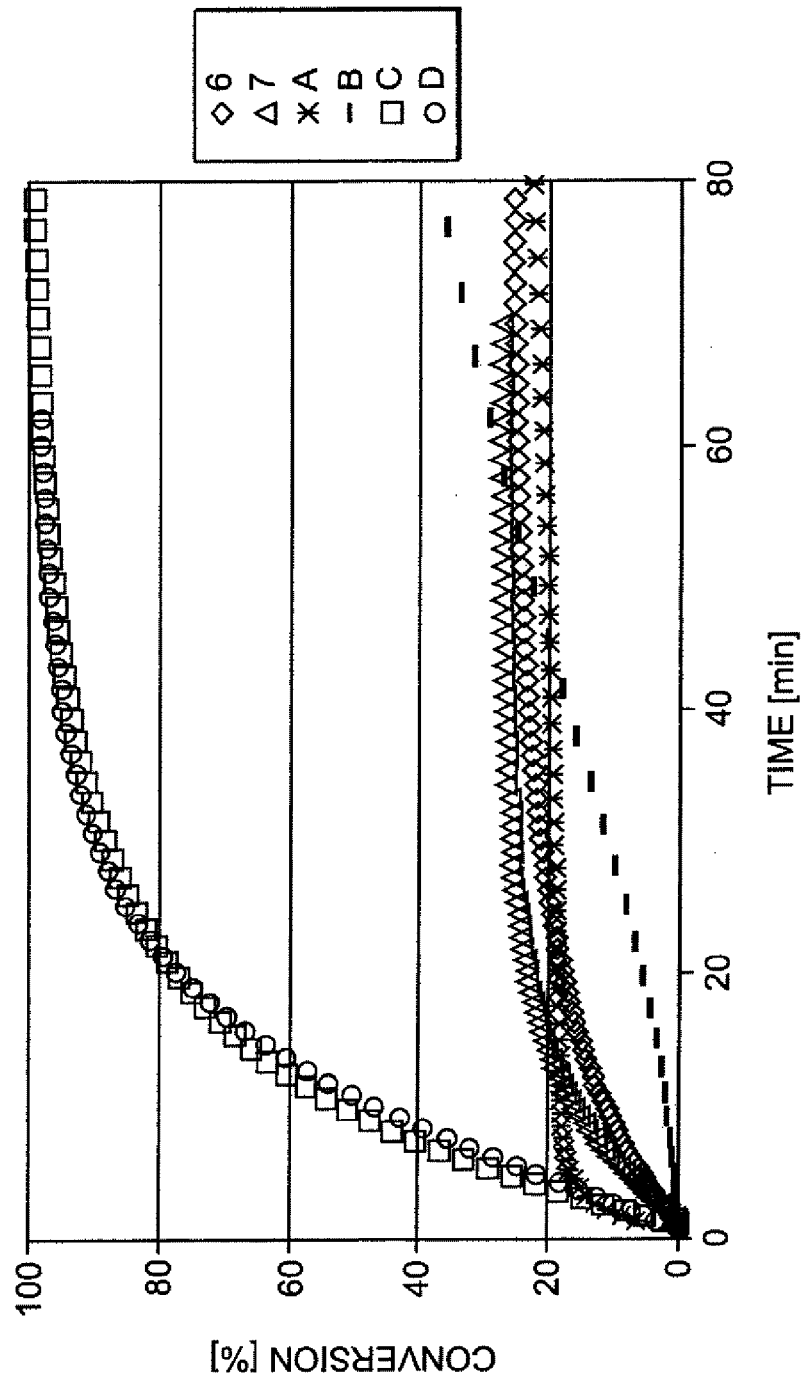
FIG. 11 shows the results of a ring-closing metathesis reaction of diethylallylmethallyl malonate to a trisubstituted cycloalkene at 30° C. (1% catalyst loading) using catalysts 6-7.
Figure 12:
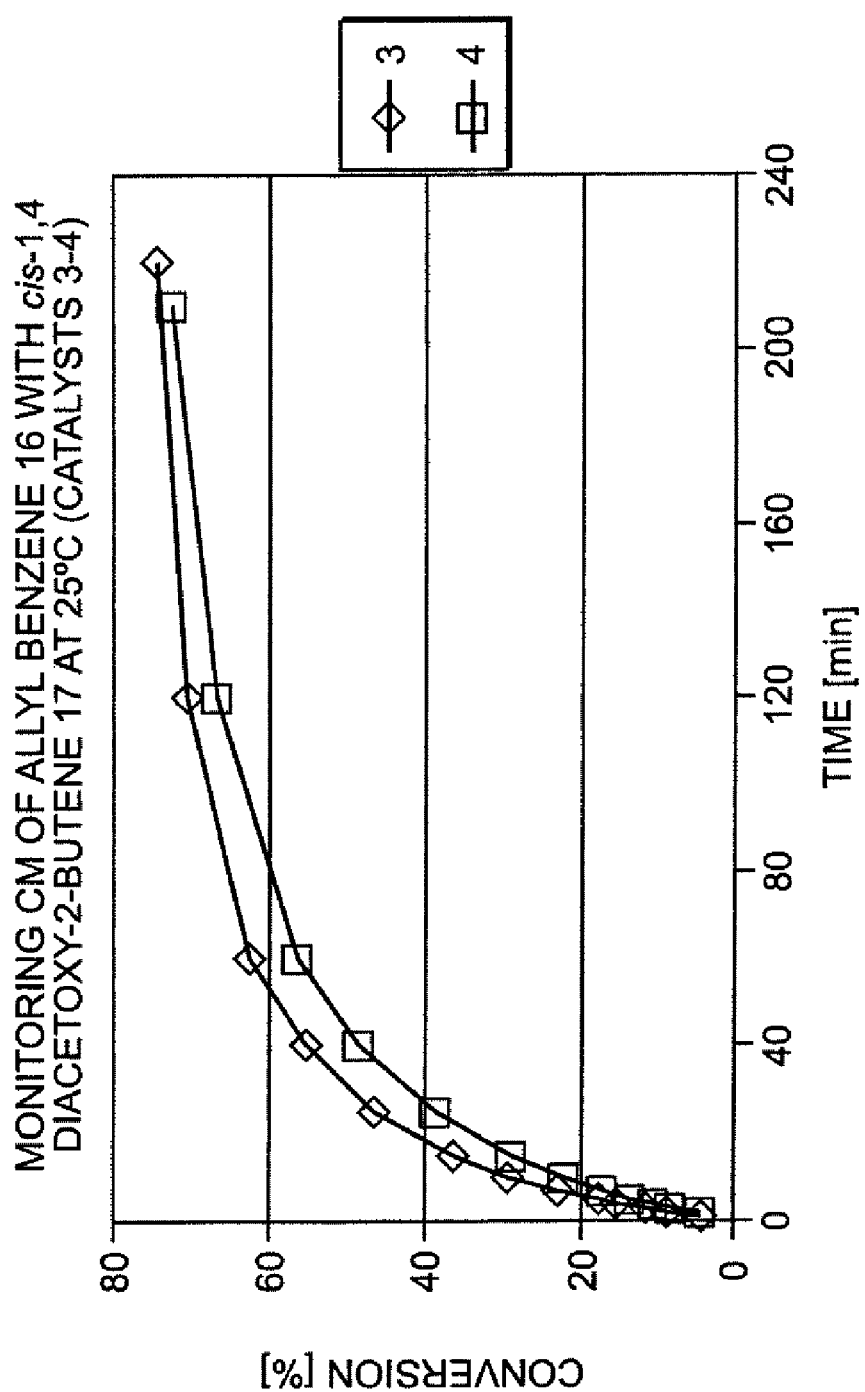
FIG. 12 shows the results of a cross-metathesis reaction of allyl benzene with cis-1,4-diacetoxy-2-butene at 25° C. (1% catalyst loading) using catalysts 3-4.
Figure 13:
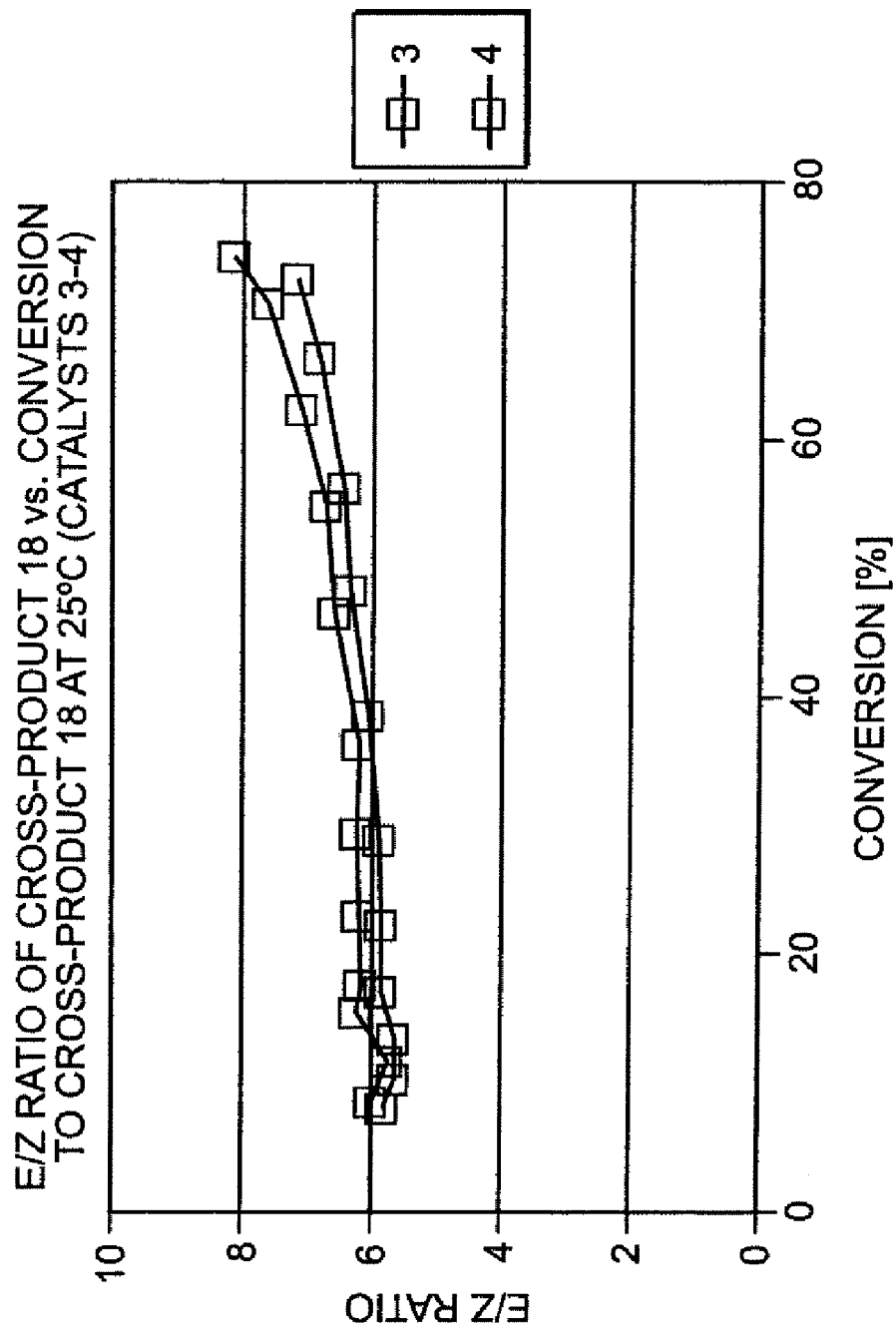
FIG. 13 depicts the E/Z ratio of the cross-metathesis reaction of allyl benzene with cis-1,4-diacetoxy-2-butene against the conversion to the cross-product at 25° C. (5% catalyst loading) using catalysts 3-4.

An NMR tube with a screw-cap septum top was charged inside a glovebox with catalyst stock solution B (200 μL, 0.80 μmol, 1.0 mmol % or 500 μL, 2 μmol, 2.5 mol %) and $C_6D_6$ (or $CD_2Cl_2$) (600 or 300 μL respectively). The sample was equilibrated at 30, 50, or 60° C. in the NMR probe before 14 (20.5 μL, 20.4 mg, 0.080 mmol, 0.1 M) was added via syringe. Data points were collected over an appropriate period of time using the Varian array function. The conversion to 15 was determined by comparing the ratio of the integrals of the methylene protons in the starting material, δ 2.91 (s), 2.88 (dt), with those in the product, δ 3.15 (s), 3.05 (m) (These are the chemical shifts in $C_6D_6$. In $CD_2Cl_2$, the corresponding chemical shifts are: δ 2.67 (s), 2.64 (dt) for the starting material, and δ 2.93 (s), 2.88 (m) for the product). FIG. 10 shows the results RCM of diethylallylmethallyl malonate (14) using catalysts 1-5, and FIG. 11 shows the results RCM of diethylallylmethallyl malonate (14) using catalysts 6-7.

Example 3(c)

Cross Metathesis of allylbenzene (16) with cis-1,4-diacetoxy-2-butene (17)

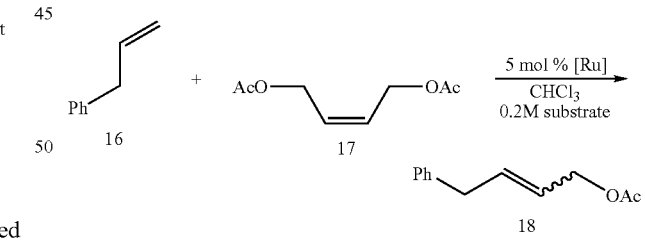

Allylbenzene (1.00 mL, 7.55 mmol) and tridecane (internal standard, 0.920 mL, 3.77 mmol) were combined in a flame-dried, 4 mL vial under an atmosphere of argon. The mixture was stirred before taking a $t_0$ timepoint. The catalyst (10 mmol) and $CDCl_3$ (1 mL) were added in a 4 mL vial in a glove box. The vial was taken out of the glove box and cis-1,4-Diacetoxy-2-butene (64 μL, 0.40 mmol) and the allylbenzene/tridecane mixture (51 μL; 0.20 mmol 14+0.10 mmol tridecane) were then added simultaneously via syringe. The reaction was allowed to stir at 25 or 60° C. Aliquots were taken at the specified time periods. Samples for GC analysis were obtained by adding a 30 μL reaction aliquot to 500 μL of

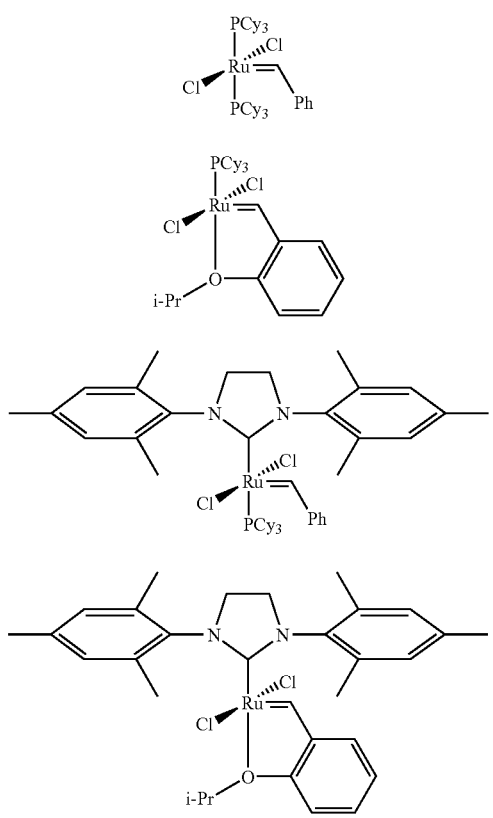

Example 3(a)

RCM of Diethyldiallyl Malonate (12)

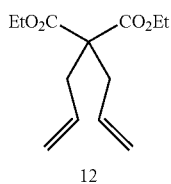

An NMR tube with a screw-cap septum top was charged inside a glovebox with catalyst stock solution B (200 μL, 0.80 μmol, 1.0 mol % or 500 μL, 2 μmol, 2.5 mol %) and $C_6D_6$ (or $CD_2Cl_2$) (600 or 300 μl respectively). The sample was equilibrated at 30, 50, or 60° C. in the NMR probe before 12 (19.3 μL, 19.2 mg, 0.080 mmol, 0.1 M) was added via syringe. Data points were collected over an appropriate period of time using the Varian array function. The conversion to 13 was determined by comparing the ratio of the integrals of the methylene protons in the starting material, δ 2.83 (dt), with those in the product, δ 3.13 (s) (These are the chemical shifts in $C_6D_6$. In $CD_2Cl_2$ the corresponding chemical shifts are: δ 2.61 (dt) and δ 2.98 (s)). FIGS. 5-8 show the results RCM of diethyla 3M solution of ethyl vinyl ether in dichloromethane. The sample was shaken, allowed to stand for 5 min, and then analyzed via GC.

Figure 14:
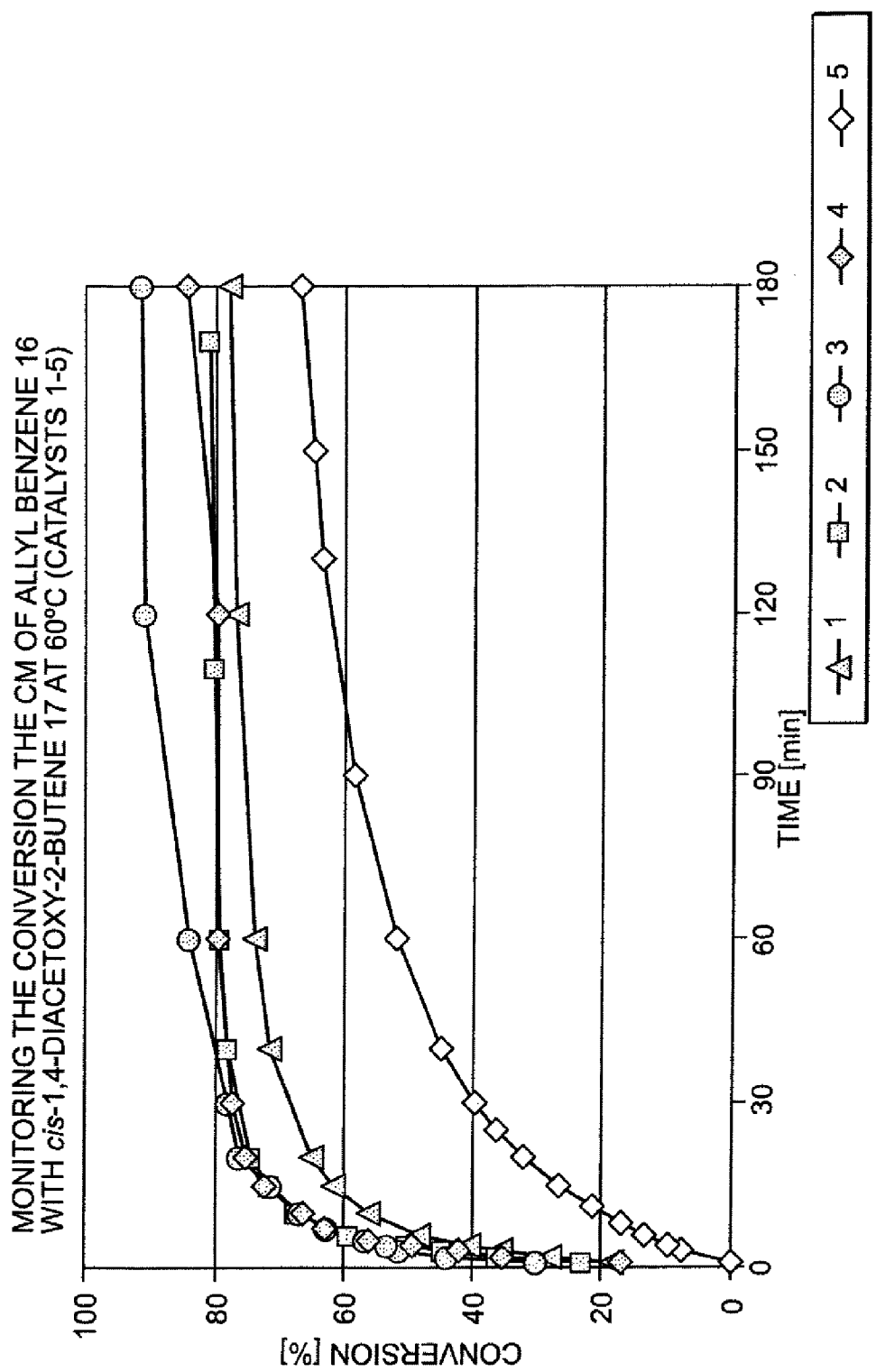
FIG. 14 shows the results of a cross-metathesis reaction of allyl benzene with cis-1,4-diacetoxy-2-butene at 60° C. (5% catalyst loading) using catalysts 3-5.
Figure 15:
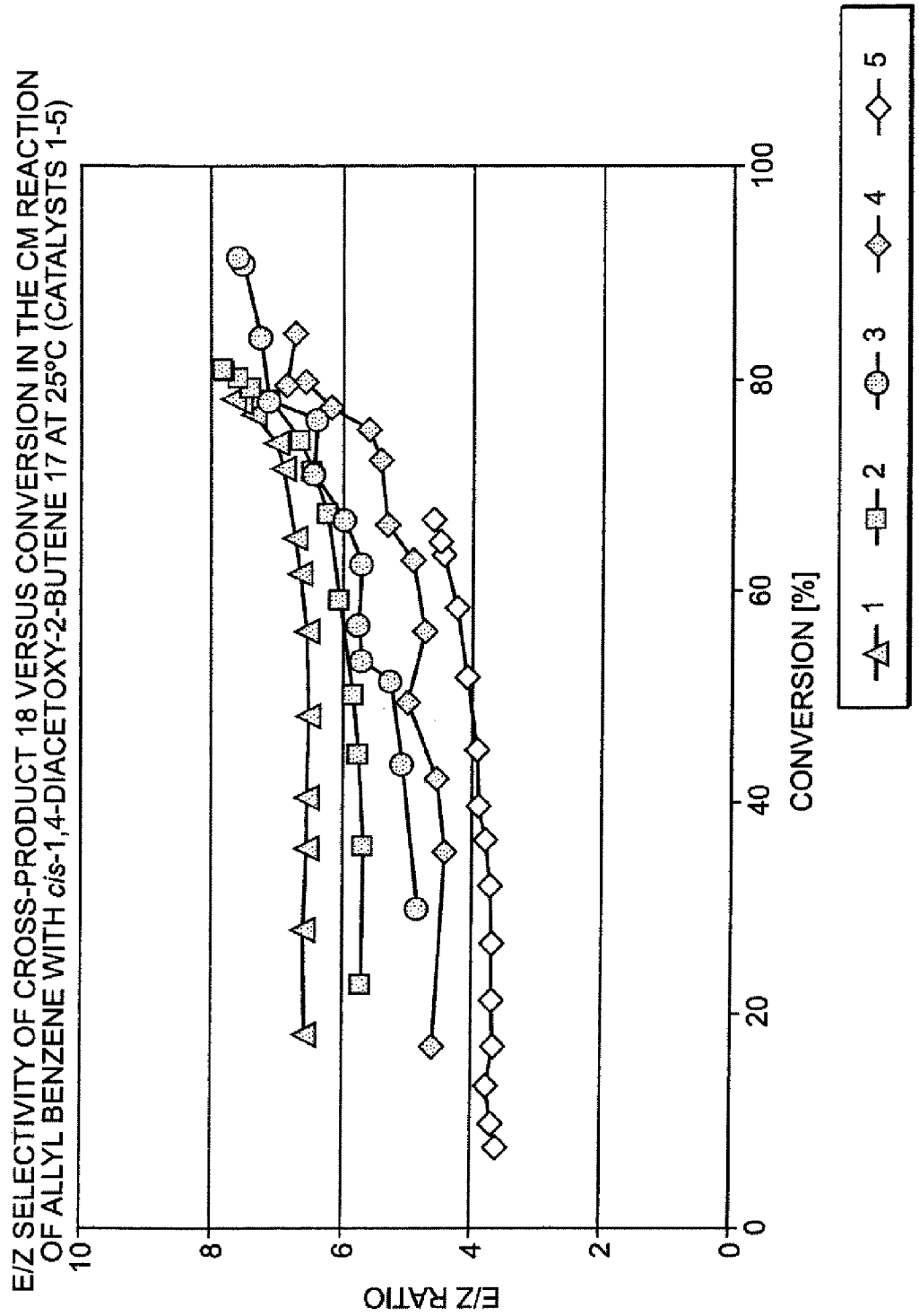
FIG. 15 depicts the E/Z ratio of the cross-metathesis reaction of allyl benzene with cis-1,4-diacetoxy-2-butene against the conversion to the cross-product at 60° C. (5% catalyst loading) using catalysts 3-5.

FIGS. 12-15 show the results of catalyzing the CM of allyl benzene (16) with cis-1,4-diacetoxy-2-butene (17) using catalysts 3-5. As seen in FIG. 14, catalysts 2 and 4 demonstrated about the same reactivity, while catalyst 3 was shown to be slightly more efficient, affording a higher yield of the desired cross-product. The catalysts also produce more Z-olefin upon increasing the bulkiness of the N-aryl substituents of the thiazole-2-ylidene ligand, as illustrated in FIG. 15. Increasing the bulkiness of the N-aryl group on the thiazole-2-ylidene ligand, the catalysts become more Z-selective with complex 5 being the most selective of all, affording an E/Z ratio that is smaller than 4 for up to 50% product yield.

Example 3(d)

ROMP of 1,5-cyclooctadiene (19)

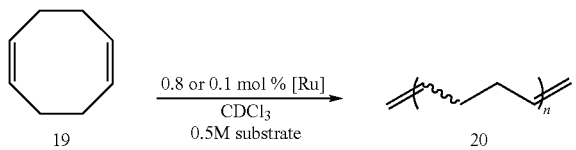

Figure 16:
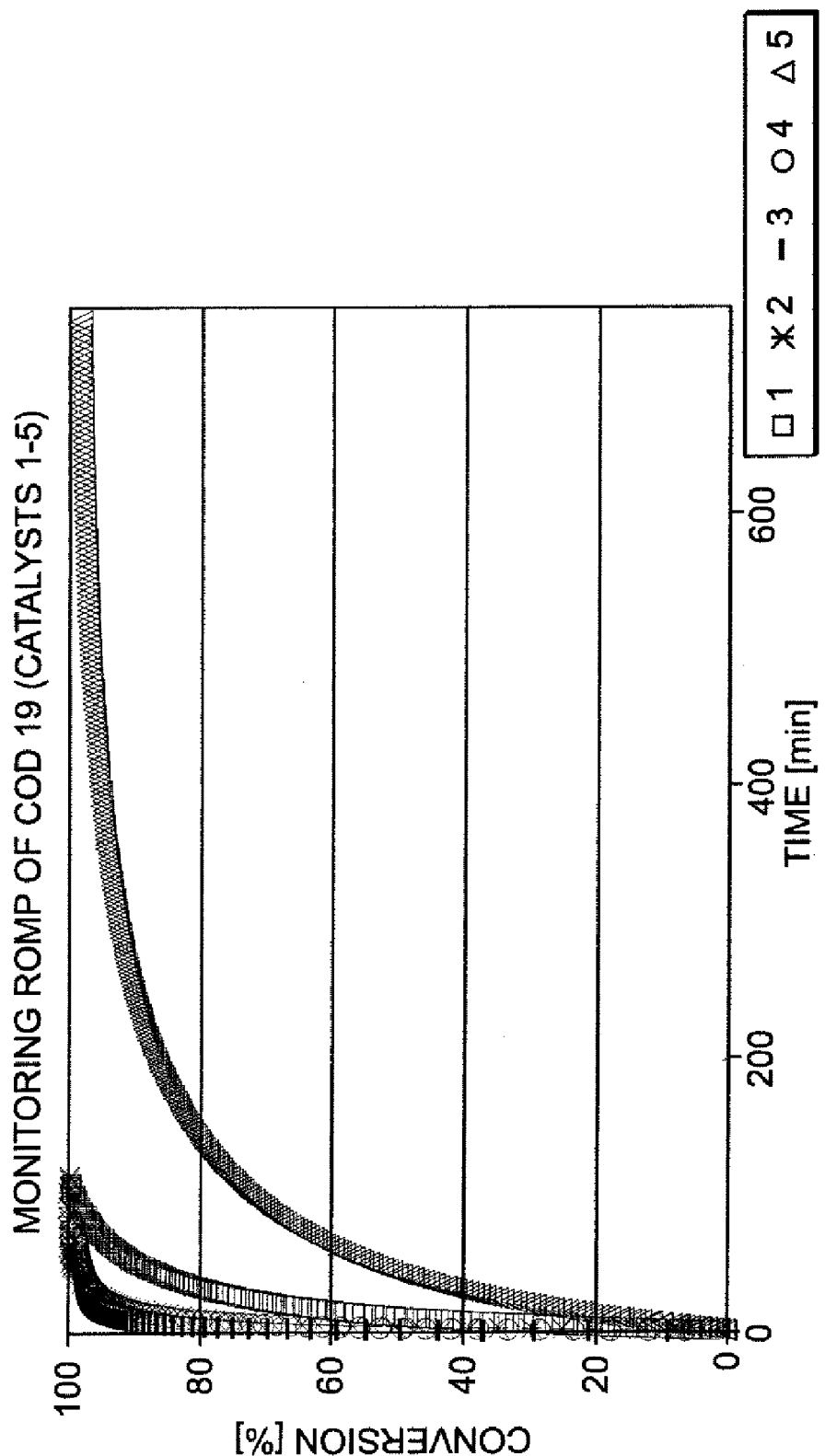
FIG. 16 shows the results of a ring-opening metathesis polymerization of 1,5-cyclooctadiene at 60° C. (0.8% catalyst loading) using catalyst 1-5.
Figure 17:
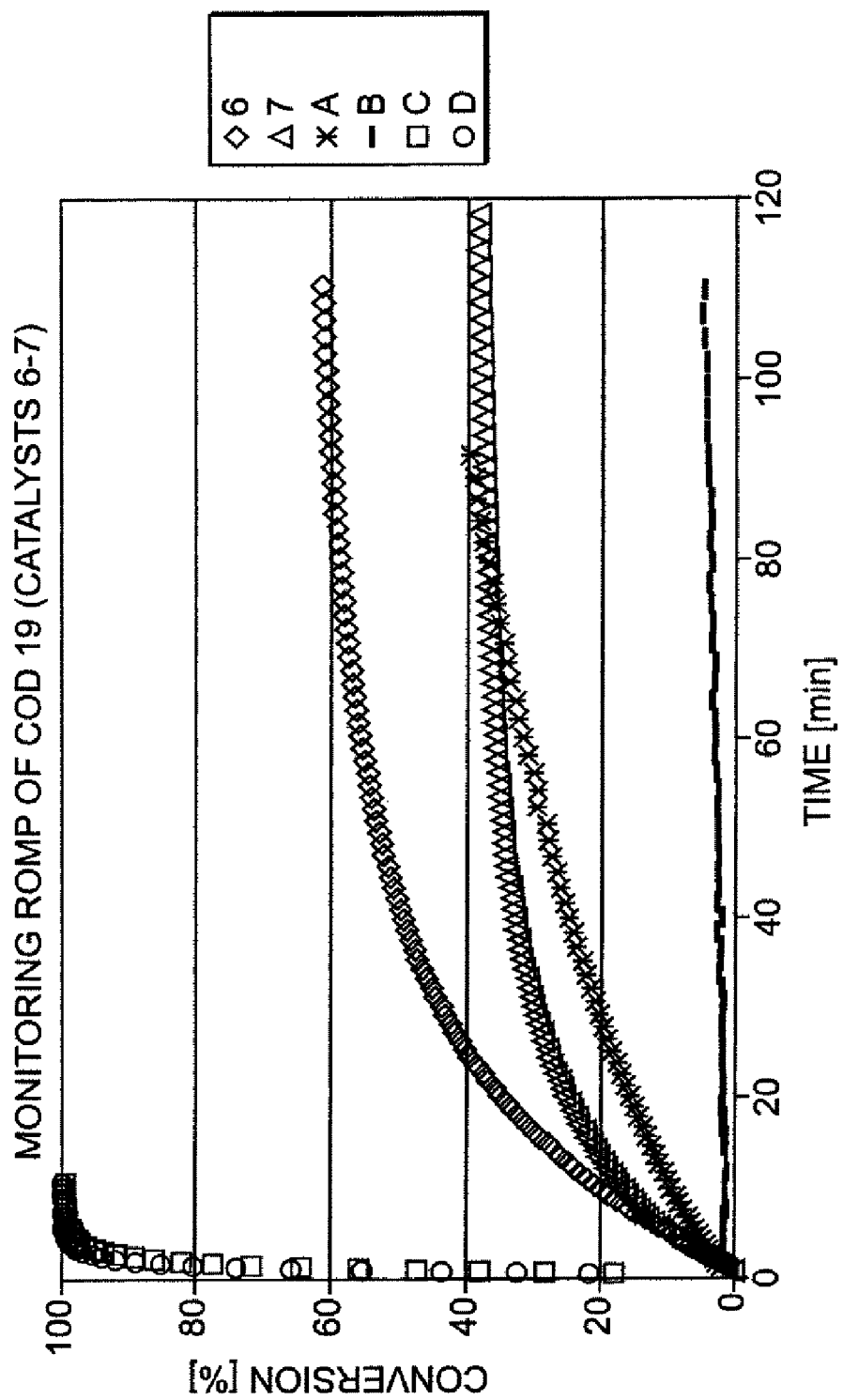
FIG. 17 shows the results of a ring-opening metathesis polymerization of 1,5-cyclooctadiene at 30° C. (0.1% catalyst loading) using catalyst 6-7.

An NMR tube with a screw-cap septum top was charged inside a glovebox with a catalyst stock solution in $CD_2Cl_2$ or $CDCl_3$ (0.004 M, 800 µL, 3.2 µmol, 0.8 mol % or 100 µL, of the 0.004 M stock solution, 0.1 mol %, along with 700 µL solvent). The sample was equilibrated at 30 or 60° C. in the NMR probe before 19 (49.1 µL, 43.3 mg, 0.40 mmol, 0.5 M) was added via syringe. Data points were collected over an appropriate period of time using the Varian array function. The conversion to 20 was determined by comparing the ratio of the integrals of the methylene protons in the starting material, δ 2.31 (m), with those in the product, δ 2.05 (br m), 2.00 (br m). FIG. 16 shows the ROMP of 1,5-cyclooctadiene (19) using catalysts 1-5 at 30° C. FIG. 17 shows the ROMP of 1,5-cyclooctadiene (19) using catalysts 6-7 at 60° C.

Example 3(e)

Macrocyclic Ring-Closing Metathesis of Diene 21

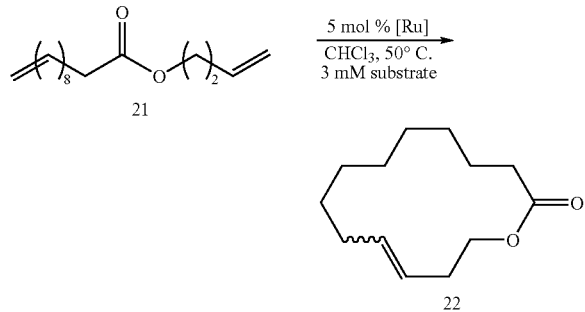

14-membered lactone 21 (410 µL, 1.5 mmol) and tridecane (internal standard, 500 µL, 2.05 mmol) were combined in a flame-dried, 4 mL vial under an atmosphere of argon. The mixture was stirred before taking a $t_0$ time point. The catalyst (1.5 µmol) and dry, degassed $ClCH_2CH_2Cl$ (6 mL) were added in a 20-mL vial in a glovebox. The vial was taken out of the glovebox and equilibrated at 50° C. for 5 minutes under argon, and the 14-membered lactone/tridecane mixture (18 µl) was then added via syringe. The reaction was allowed to stir at 50° C. Samples for GC analysis were obtained by adding a 400-µL reaction aliquot to 100 µL of a 3M solution of ethyl vinyl ether in dichloromethane. The sample was shaken, allowed to stand for at least 5 minutes, and then analyzed via GC.

Figure 18:
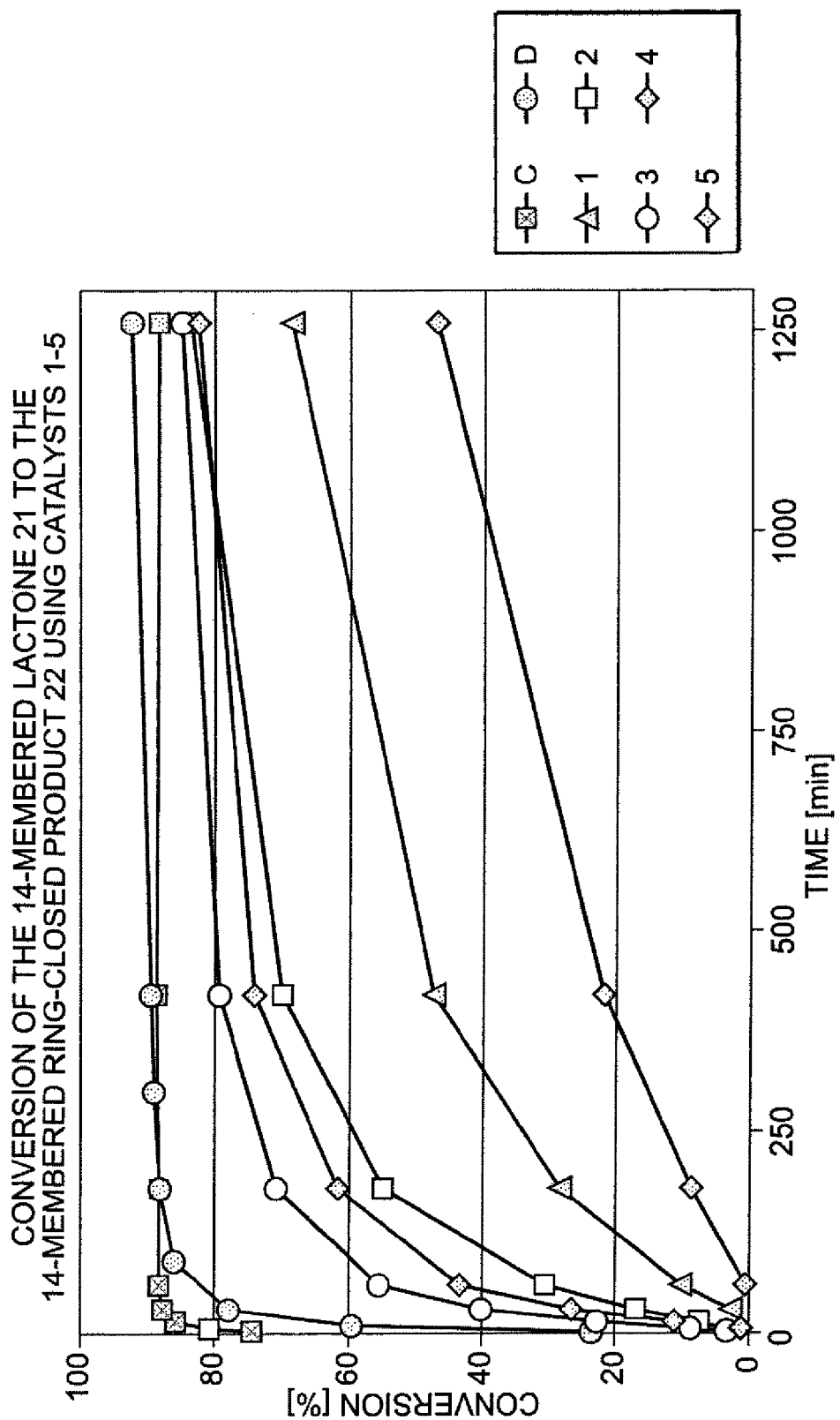
FIG. 18 shows the results of a ring-closing metathesis reaction of a lactone to the 14-membered product using catalysts 1-5.
Figure 19:
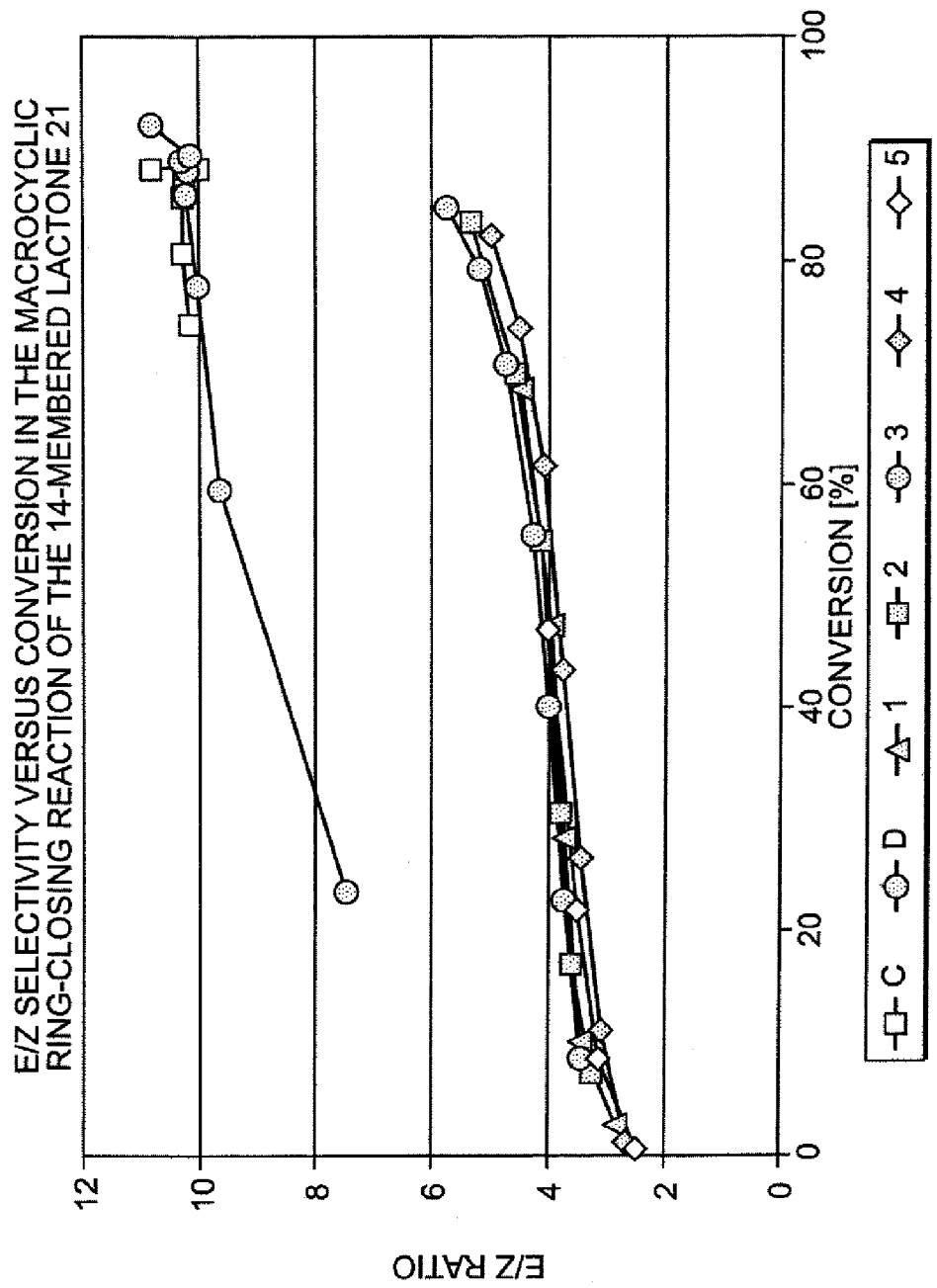
FIG. 19 depicts the E/Z selectivity of the macrocyclic ring-closing metathesis reaction of a lactone to the 14-membered product using catalysts 1-5.

The catalytic activity of catalysts 1-5 in the macrocyclic ring-closing of the 14-membered lactone 21 was analyzed in FIGS. 18 and 19. As shown in FIG. 18, catalysts 2-4 were the most reactive catalysts in this family, showing reactivity comparable to that of conventional catalysts C and D. As shown in FIG. 19, catalysts 1-5 display almost identical stereoselectivity in this reaction, producing macrocyclic product 22 with an E/Z ratio that begins at ~3 and finally reaches the value of ~6 at 85% conversion. Interestingly, the E/Z profile of catalysts 1-5 is different than that of catalysts C and D and more similar to the stereoselectivity displayed by catalyst A in the same reaction. An analysis of catalyst A may be found in Lee et al., *Org. Lett.*, 2, 2145-2147, herein incorporated by reference in its entirety.

The catalysts of this invention have been shown to efficiently catalyze a variety of metathesis reactions. The examples show the RCM reactions of diethyldiallyl malonate (12, FIGS. 5-9) and diethylallylmethallyl malonate (14, FIGS. 10-11); the CM reactions of allyl benzene (16) with cis-1,4-diacetoxy-2-butene (17) (FIGS. 12-15); the ROMP of 1,5-cyclooctadiene (19) (FIGS. 16-17); and the macrocyclic RCM of diene 21 (FIGS. 18-19). More significantly, as illustrated by the linear logarithmic plot of diene concentration vs. time in the RCM reactions of 12 catalyzed by catalysts 3-5, at 1% catalyst loading, at 60° C. (FIG. 7), these RCM reactions follow pseudo-first order kinetics, namely catalysts 3-5 are unexpectedly stable.

We claim:

1. A compound, having general formula (I):

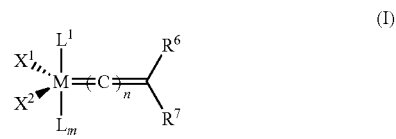

wherein:

M is Ru or Os;

n is 0, 1 or 2;

$X^1$ and $X^2$ are independently anionic ligands;

L is any neutral 2-electron donor ligand;

m is 1 or 2;

$R^6$ and $R^7$ are each independently hydrogen or a substituted or unsubstituted group selected from the group consisting of $C_1$-$C_{20}$ alkyl, $C_2$-$C_{20}$ alkenyl, $C_2$-$C_{20}$ alkynyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl, and $C_1$-$C_{20}$ alkylsulfinyl; and $L^1$ is a thiazol-2-ylidene ligand of formula (II):

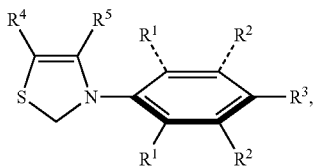

wherein
- $R^4$ and $R^5$ are each independently H, a substituted or unsubstituted $C_1$-$C_8$ alkyl group, substituted or unsubstituted aryl, or, together with the carbons carrying them, form a substituted or unsubstituted, fused 4-8 membered carbocylic ring or a substituted or unsubstituted, fused aromatic ring; and
- $R^1$, $R^2$, and $R^3$ are collectively defined as combination (a) or combination (b):
  - (a) each $R^1$ is independently a primary or secondary $C_1$-$C_4$ alkyl group; each $R^2$ is independently H; and $R^3$ is independently H, a substituted or unsubstituted $C_1$-$C_8$ alkyl group, substituted or unsubstituted phenyl, substituted or unsubstituted naphthyl, or substituted or unsubstituted anthracenyl, or a functional group selected from the group consisting of halo, hydroxyl, sulfhydryl, cyano, cyanato, thiocyanato, amino, nitro, nitroso, sulfa, sulfonato, boryl, borono, phosphono, phosphonato, phosphinato, phospho, phosphino, and silyloxy; or
  - (b) each $R^1$ is H; each $R^2$ is independently H, a substituted or unsubstituted $C_1$-$C_8$ alkyl group, substituted or unsubstituted phenyl, substituted or unsubstituted naphthyl, or substituted or unsubstituted anthracenyl; and $R^3$ is H.

2. The compound of claim 1, wherein $R^1$, $R^2$, and $R^3$ in $L^1$ is defined by combination (a), wherein each $R^1$ is methyl, ethyl, or iso-propyl; and $R^3$ is H, iso-butyl, tert-butyl, neopentyl, neohexyl, or phenyl.

3. The compound of claim 2, wherein each $R^1$ is methyl or ethyl; and $R^3$ is H.

4. The compound of claim 1, wherein $R^1$, $R^2$, and $R^3$ in $L^1$ is defined by combination (b), wherein each $R^2$ is a secondary or tertiary $C_3$-$C_{10}$ alkyl or aryl; and $R^3$ is H, iso-butyl, tert-butyl, neopentyl, neohexyl, or phenyl.

5. The compound of claim 4, wherein each $R^2$ is iso-butyl, tert-butyl, neopentyl, neohexyl, or phenyl; and $R^3$ is H.

6. The compound of claim 1, wherein $R^4$ and $R^5$ are independently H or $C_1$-$C_4$ alkyl, or fused cyclohexyl or phenyl.

7. The compound of claim 1, wherein $X^1$ and $X^2$ are independently selected from the group consisting of halide, $C_1$-$C_{20}$ alkyl, aryl, $C_1$-$C_{20}$ alkoxide, aryloxide, $C_3$-$C_{20}$ alkyldiketonate, aryldiketonate, $C_1$-$C_{20}$ carboxylate, arylsulfonate, $C_1$-$C_{20}$ alkylsulfonate, $C_1$-$C_{20}$ alkylthio, $C_1$-$C_{20}$ alkylsulfonyl, and $C_1$-$C_{20}$ alkylsulfinyl.

8. The compound of claim 7, wherein $X^1$ and $X^2$ are independently selected from the group consisting of halide, benzoate, $C_1$-$C_5$ carboxylate, $C_1$-$C_5$ alkyl, phenoxy, $C_1$-$C_5$ alkoxy, $C_1$-$C_5$ alkylthio, aryl, and $C_1$-$C_5$ alkylsulfonate.

9. The compound of claim 8, wherein $X^1$ and $X^2$ are independently selected from the group consisting of halide, $CF_3CO_2$, $CH_3$, $CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate.

10. The compound of claim 9, wherein $X^1$ and $X^2$ are each chloride.

11. The compound of claim 1, wherein $R^6$ is hydrogen, substituted or unsubstituted $C_1$-$C_5$ alkyl, or substituted or unsubstituted aryl; and $R^7$ is substituted or unsubstituted $C_1$-$C_{20}$ alkyl, substituted or unsubstituted $C_2$-$C_{20}$ alkenyl, or substituted or unsubstituted aryl.

12. The compound of claim 11, wherein $R^6$ is hydrogen, and $R^7$ is phenyl or vinyl, optionally substituted with one or more moieties selected from the group consisting of $C_1$-$C_5$ alkyl, $C_1$-$C_5$ alkoxy, phenyl, chloride, bromide, iodide, fluoride, —$NO_2$, and —$NMe_2$.

13. The compound of claim 12, wherein $R^7$ is phenyl or —C=C(CH$_3$)$_2$.

14. The compound of claim 1, wherein m is 1, n is 0, and L is linked to $R^7$ forming a chelating carbene ligand.

15. The compound of claim 14, wherein L is linked to $R^7$ through a spacer moiety, where the space moiety is substituted or unsubstituted alkyl group, a substituted or unsubstituted cycloalkyl group, or a substituted or unsubstituted aryl group.

16. The compound of claim 14, wherein M is Ru, and L and $R^7$ are linked to form a complex selected from the group consisting of

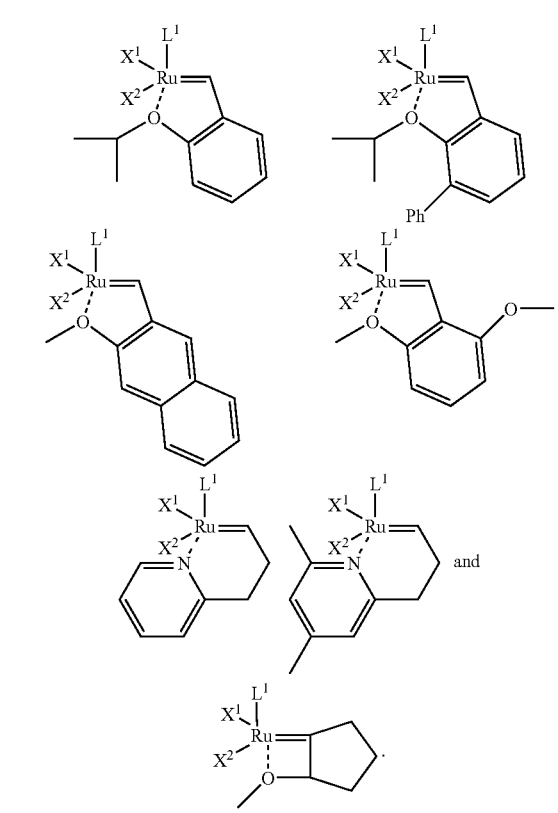

17. The compound of claim 1, wherein m is 2, and each L ligand is independently pyridine or substituted pyridine.

18. The compound of claim 1, wherein L is selected from the group consisting of phosphine, sulfonated phosphine, phosphite, phosphinite, phosphonite, arsine, stibine, ether, amine, amide, imine, sulfoxide, carboxyl, nitrosyl, pyridine, thioether, and $L^1$.

19. The compound of claim 18, wherein L is a phosphine of the formula PR'R"R'", where R', R", and R'" are each independently aryl; $C_1$-$C_{10}$ alkyl; or $C_3$-$C_6$ cycloalkyl.

20. The compound of claim 19, wherein L is selected from the group consisting of P(cyclohexyl)$_3$, P(cyclopentyl)$_3$, P(isopropyl)$_3$, and P(phenyl)$_3$.

21. The compound of claim 1, having the formula:

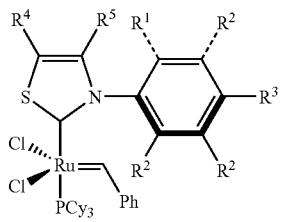

wherein R$^1$, R$^2$, R$^3$, R$^4$, and R$^5$ are defined in claim 1.

22. The compound of claim 1, having the formula:

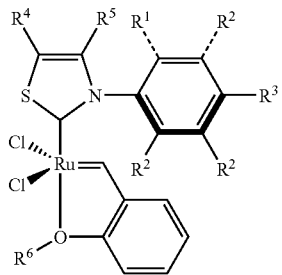

wherein R$^1$, R$^2$, R$^3$, R$^4$, and R$^5$ are defined in claim 1, and wherein R$^6$ is a C$_1$-C$_4$ alkyl.

23. The compound of claim 1, wherein the compound is selected from the group consisting of:

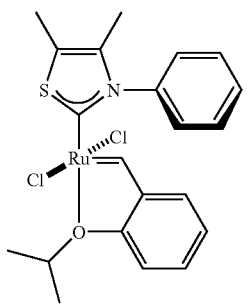
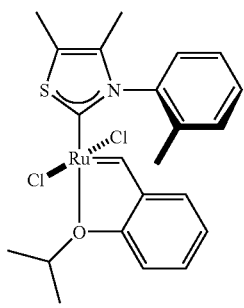
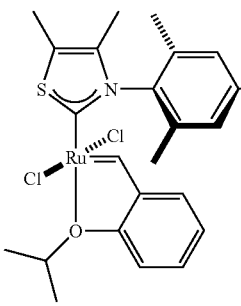
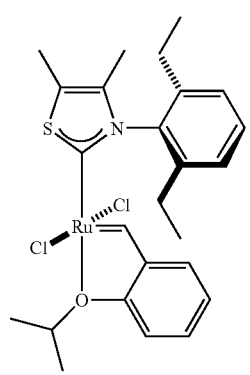

-continued

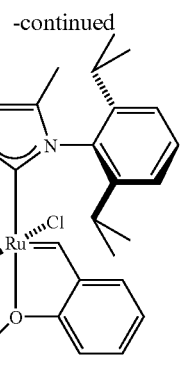

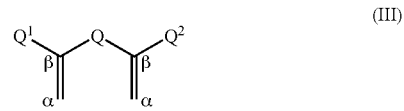

24. A method of preparing a tetra-substituted cyclic olefin through a ring-closing metathesis reaction, comprising contacting an olefinic compound with a compound of claim 1 under metathesis conditions to form a cyclic tetra-substituted olefin, wherein the olefinic compound has at least two terminal olefins that are substituted at the beta-carbon of each terminal olefin.

25. The method of claim 24, wherein the olefinic compound has a structure according to general formula (III):

$$Q^1\underset{\alpha}{\overset{\beta}{\diagup\!\!\!\diagdown}}\;Q\;\underset{\alpha}{\overset{\beta}{\diagdown\!\!\!\diagup}}Q^2 \qquad (III)$$

wherein
Q is selected from the group consisting of hydrocarbylene, substituted hydrocarbylene, heteroatom-containing hydrocarbylene, and substituted heteroatom-containing hydrocarbylene;
Q$^1$ and Q$^2$ are independently selected from the group consisting of hydrogen, hydrocarbyl, substituted hydrocarbyl, heteroatom-containing hydrocarbyl, substituted heteroatom-containing hydrocarbyl, halide, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy
with the proviso that Q$^1$ and Q$^2$ cannot both be hydrogen.

26. The method of claim 25, wherein neither Q$^1$ nor Q$^2$ are hydrogen.

27. A method of preparing a tri-substituted olefin or a di-substituted olefin that is further substituted at the allylic carbon, through a cross-metathesis reaction, comprising contacting two olefins with a compound of claim 1 under metathesis conditions to form a tri-substituted olefin, wherein the first olefin is monosubstituted at the β-carbon and either unsubstituted or monosubstituted at the α-carbon, and the second olefin is either disubstituted at the β-carbon or monosubstituted at the β-carbon with a further substitution at the allylic carbon, and either monosubstituted or unsubstituted at the α-carbon.

28. The method of claim 27, wherein the tri-substituted olefin has the formula $Q^1Q^2C=CHQ^3$, wherein $Q^1$, $Q^2$, and $Q^3$ are independently selected from the group consisting of hydrocarbyl, substituted hydrocarbyl, heteroatom-containing hydrocarbyl, substituted heteroatom-containing hydrocarbyl, halide, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy, wherein $Q^1$, $Q^2$, and/or $Q^3$ may be linked as part of a cyclic olefin.

29. The method of claim 27, wherein the di-substituted olefin has the formula $Q^1Q^2C=CH_2$ or $Q^1HC=CHQ^2$, wherein $Q^1$ and $Q^2$ are independently selected from the group consisting of hydrocarbyl, substituted hydrocarbyl, heteroatom-containing hydrocarbyl, substituted heteroatom-containing hydrocarbyl, halide, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy, wherein $Q^1$ and $Q^2$ may be linked as part of a cyclic olefin.

30. The method of claim 27, wherein the di-substituted olefin having a further substitution at the allylic carbon has the formula $Q^1HC=CHCQ^2Q^3Q^4$, wherein $Q^1$, $Q^2$, $Q^3$, and $Q^4$ are independently selected from the group consisting of hydrocarbyl, substituted hydrocarbyl, heteroatom-containing hydrocarbyl, substituted heteroatom-containing hydrocarbyl, halide, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy, wherein $Q^1$, $Q^2$, $Q^3$ and/or $Q^4$ may be linked as part of a cyclic olefin.

31. A method for synthesizing a polymer using a ring-opening metathesis polymerization reaction, comprising contacting a cyclic olefin with a compound of claim 1.

32. A method for synthesizing a cyclic olefin by ring-closing metathesis, comprising contacting an acyclic diene in the presence of a compound of claim 1 to yield a cyclic olefin.

33. The method of claim 32, wherein the cyclic olefin is macrocyclic olefin.

* * * * *